(12) United States Patent
Huang et al.

(10) Patent No.: US 12,195,545 B2
(45) Date of Patent: Jan. 14, 2025

(54) ANTI-OX40 MONOCLONAL ANTIBODY AND APPLICATION THEREOF

(71) Applicant: HANX BIOPHARMACEUTICS, INC, Hubei (CN)

(72) Inventors: Ying Huang, Hubei (CN); Faming Zhang, Hubei (CN); Hang Ke, Hubei (CN)

(73) Assignee: HANX BIOPHARMACEUTICS, INC, Hubei (CN)

( * ) Notice: Subject to any disclaimer, the term of this patent is extended or adjusted under 35 U.S.C. 154(b) by 839 days.

(21) Appl. No.: 17/418,145

(22) PCT Filed: Dec. 25, 2018

(86) PCT No.: PCT/CN2018/123393
§ 371 (c)(1),
(2) Date: Jun. 24, 2021

(87) PCT Pub. No.: WO2020/132857
PCT Pub. Date: Jul. 2, 2020

(65) Prior Publication Data
US 2022/0017632 A1    Jan. 20, 2022

(51) Int. Cl.
| C07K 16/28 | (2006.01) |
| A61K 39/00 | (2006.01) |
| A61K 45/06 | (2006.01) |
| A61P 35/00 | (2006.01) |
| C07K 16/30 | (2006.01) |
| C12N 15/85 | (2006.01) |

(52) U.S. Cl.
CPC .. *C07K 16/2878* (2013.01); *A61K 39/001129* (2018.08); *A61K 45/06* (2013.01); *A61P 35/00* (2018.01); *C07K 16/30* (2013.01); *C12N 15/85* (2013.01); *A61K 2039/505* (2013.01)

(58) Field of Classification Search
CPC ............... C07K 16/2878; C07K 16/30; C07K 2317/33; C07K 2317/75; C07K 2317/92; A61K 45/06; A61K 2039/505; A61K 39/001129; A61P 35/00; A61P 37/04; C12N 15/85
See application file for complete search history.

(56) References Cited

U.S. PATENT DOCUMENTS

| 2004/0137000 A1* | 7/2004 | Lynn | A61P 31/18 435/339.1 |
| 2005/0281823 A1* | 12/2005 | Gately | C07K 16/244 424/145.1 |
| 2012/0027773 A1* | 2/2012 | Whalen | C07K 16/2896 435/69.6 |
| 2020/0165630 A1* | 5/2020 | Paul | C12N 15/86 |

FOREIGN PATENT DOCUMENTS

| CN | 103717263 | 4/2014 |
| CN | 108137686 | 6/2018 |
| CN | 108218990 | 6/2018 |
| JP | 2017514461 A | 6/2017 |
| JP | 2018520647 A | 8/2018 |
| WO | 2013008171 A1 | 1/2013 |
| WO | 2013028231 A1 | 2/2013 |
| WO | 2015153513 A1 | 10/2015 |
| WO | 2016057667 A1 | 4/2016 |
| WO | 2016196228 A1 | 12/2016 |
| WO | 2018112346 A1 | 6/2018 |

OTHER PUBLICATIONS

Almagro JC et. al., Progress and Challenges in the Design and Clinical Development of Antibodies for Cancer Therapy Front. Immunol. 2018; 8:1751 (Year: 2018).*
Chiu ML et al. Antibody Structure and Function: The Basis for Engineering Therapeutics. Antibodies 2019 8, 55, 1-80 (Year: 2019).*
Hasegawa H et al. Single amino acid substitution in LC-CDR1 induces Russell body phenotype that attenuates cellular protein synthesis through eIF2α phosphorylation and thereby downregulates IgG secretion despite operational secretory pathway traffic. (mAbs 2017, 9(5) 854-873) (Year: 2017).*
WIPO, International Search Report for PCT/CN2018/123393, Sep. 24, 2019.
Betts et al., "Chapter 14: Amino Acid Properties and Consequences of Substitutions," Bioinformatics for Geneticists, John Wiley & Sons, Ltd., 2003.
EPO, Extended European Search Report for EP Application No. 18945324.4, Jul. 14, 2022.
JPO, Office Action for JP Application No. 2021-537796, Sep. 20, 2022.

* cited by examiner

*Primary Examiner* — Karen A. Canella
*Assistant Examiner* — John J Skoko, III
(74) *Attorney, Agent, or Firm* — Hodgson Russ LLP

(57) ABSTRACT

Provided in the present invention are an anti-OX40 monoclonal antibody or an antigen-binding fragment thereof, and a corresponding isolated polynucleotide, expression vector, recombinant cell, pharmaceutical composition, and application thereof. The present antibody can be used for the treatment of cancer or autoimmune disease.

19 Claims, 5 Drawing Sheets
Specification includes a Sequence Listing.

SEQUENCE LISTING

```
<160> NUMBER OF SEQ ID NOS: 37

<210> SEQ ID NO 1
<211> LENGTH: 118
<212> TYPE: PRT
<213> ORGANISM: Artificial Sequence
<220> FEATURE:
<223> OTHER INFORMATION: Heavy chain amino acids

<400> SEQUENCE: 1

Gln Val Gln Leu Gln Gln Ser Gly Gly Gly Leu Val Lys Pro Gly Gly
1               5                   10                  15

Ser Leu Lys Leu Ser Cys Ala Ala Ser Gly Phe Thr Phe Ser Asp Tyr
            20                  25                  30

Tyr Met Tyr Trp Val Arg Gln Thr Pro Glu Lys Arg Leu Glu Trp Val
        35                  40                  45

Ala Thr Ile Ser Asp Gly Gly Ser Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Lys Ser Glu Asp Thr Ala Thr Tyr Tyr Cys
                85                  90                  95

Ala Arg Arg Gly Thr Gly Thr Gly Phe Gly Tyr Trp Gly Gln Gly Thr
            100                 105                 110

Leu Val Thr Val Ser Ala
        115

<210> SEQ ID NO 2
<211> LENGTH: 107
<212> TYPE: PRT
<213> ORGANISM: Artificial Sequence
<220> FEATURE:
<223> OTHER INFORMATION: Light chain amino acids

<400> SEQUENCE: 2

Asp Ile Val Leu Thr Gln Thr Thr Ala Ser Leu Ser Val Ser Val Gly
1               5                   10                  15

Glu Thr Val Thr Ile Thr Cys Arg Ala Ser Glu Asn Ile Tyr Ser Thr
            20                  25                  30

Leu Ala Trp Tyr Gln Gln Lys Gln Gly Lys Ser Pro Gln Leu Leu Val
        35                  40                  45

Tyr Ala Ala Thr Asn Leu Val Ala Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Ile Pro Trp
                85                  90                  95
```

```
Thr Phe Gly Gly Gly Thr Lys Leu Glu Ile Lys
            100                 105
```

<210> SEQ ID NO 3
<211> LENGTH: 117
<212> TYPE: PRT
<213> ORGANISM: Artificial Sequence
<220> FEATURE:
<223> OTHER INFORMATION: Heavy chain amino acids

<400> SEQUENCE: 3

```
Glu Val Gln Leu Gln Gln Ser Gly Pro Glu Leu Val Lys Pro Gly Ala
1               5                   10                  15

Leu Val Lys Ile Ser Cys Lys Ala Ser Gly Tyr Thr Phe Thr Asn Tyr
            20                  25                  30

Asp Ile Asn Trp Val Lys Gln Arg Pro Gly Gln Gly Leu Glu Trp Ile
        35                  40                  45

Gly Trp Ile Tyr Pro Glu Asp Gly Ser Thr Lys Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asn Ser Ala Val Tyr Phe Cys
                85                  90                  95

Ala Arg Asp Thr Arg Gly Tyr Phe Asp Tyr Trp Gly Gln Gly Thr Thr
            100                 105                 110

Leu Thr Val Ser Ser
        115
```

<210> SEQ ID NO 4
<211> LENGTH: 107
<212> TYPE: PRT
<213> ORGANISM: Artificial Sequence
<220> FEATURE:
<223> OTHER INFORMATION: Light chain amino acids

<400> SEQUENCE: 4

```
Asp Ile Val Met Thr Gln Thr Thr Ala Ile Met Ser Ala Ser Leu Gly
1               5                   10                  15

Glu Lys Val Thr Met Ser Cys Arg Ala Ser Ser Ser Val Asn Tyr Ile
            20                  25                  30

Tyr Trp Tyr Gln Gln Lys Ser Asp Ala Ser Pro Lys Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Ser Tyr Ser Leu Thr Ile Ser Ser Met Glu Gly Glu
65                  70                  75                  80

Asp Ala Ala Thr Tyr Tyr Cys Gln Gln Phe Thr Ser Ser Pro Trp Thr
                85                  90                  95

Phe Gly Gly Gly Thr Lys Leu Glu Phe Lys Arg
            100                 105
```

<210> SEQ ID NO 5
<211> LENGTH: 122
<212> TYPE: PRT
<213> ORGANISM: Artificial Sequence
<220> FEATURE:
<223> OTHER INFORMATION: Heavy chain amino acids

<400> SEQUENCE: 5

```
Gln Val Gln Leu Gln Glu Ser Gly Pro Ser His Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Leu
        35                  40                  45

Gly Tyr Ile Ser Phe Ser Gly Asn Thr Tyr Tyr Asn Pro Ser Leu Lys
50                  55                  60

Ser Arg Ile Ser Ile Ile Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
            85                  90                  95

Arg Tyr Pro Tyr Ser Tyr Ser Asn Trp Asp Tyr Ala Met Asp Tyr Trp
        100                 105                 110

Gly Gln Gly Thr Ser Val Thr Val Ser Ser
            115                 120
```

<210> SEQ ID NO 6
<211> LENGTH: 113
<212> TYPE: PRT
<213> ORGANISM: Artificial Sequence
<220> FEATURE:
<223> OTHER INFORMATION: Light chain amino acids

<400> SEQUENCE: 6

```
Asp Ile Val Met Thr Gln Ser Pro Ser Ser Leu Val Val Ser Val Gly
1               5                   10                  15

Glu Lys Val Thr Met Ser Cys Lys Ser Ser Gln Phe Leu Leu Tyr Ser
            20                  25                  30

Ser Ser Gln Lys Asn Tyr Leu Ala Trp Tyr Gln Gln Lys Pro Gly Gln
        35                  40                  45

Ser Pro Gln Leu Leu Ile Tyr Trp Ala Ser Thr Arg Glu Ser Gly Val
50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys His Gln
            85                  90                  95

Tyr Tyr Ser Tyr Pro Leu Thr Phe Gly Ala Gly Thr Lys Leu Glu Leu
        100                 105                 110

Lys
```

<210> SEQ ID NO 7
<211> LENGTH: 115
<212> TYPE: PRT
<213> ORGANISM: Artificial Sequence
<220> FEATURE:
<223> OTHER INFORMATION: Heavy chain amino acids

<400> SEQUENCE: 7

```
Glu Val Lys Leu Glu Glu Ser Gly Pro Ser Leu Val Lys Pro Ser Gln
1               5                   10                  15

Thr Leu Ser Leu Thr Cys Ser Val Ser Gly Asp Ser Ile Thr Ile Gly
            20                  25                  30

Phe Trp Asn Trp Ile Arg Lys Phe Pro Gly Asn Lys Leu Glu Tyr Met
        35                  40                  45

Gly Tyr Ile Asn Tyr Ser Gly Ser Ser Tyr Tyr Asn Pro Ser Leu Lys
50                  55                  60
```

```
Ser Arg Ile Ser Ile Thr Arg Asp Thr Ser Lys Asn Gln Tyr Tyr Leu
 65                  70                  75                  80

Gln Leu Asn Ser Val Thr Pro Glu Asp Thr Ala Thr Tyr Tyr Cys Ala
                 85                  90                  95

Arg Ser Gly Thr Asp Leu Asp Tyr Trp Gly Gln Gly Thr Thr Leu Thr
            100                 105                 110

Val Ser Ser
        115
```

<210> SEQ ID NO 8
<211> LENGTH: 113
<212> TYPE: PRT
<213> ORGANISM: Artificial Sequence
<220> FEATURE:
<223> OTHER INFORMATION: Light chain amino acids

<400> SEQUENCE: 8

```
Asp Ile Val Leu Thr Gln Ser Pro Leu Thr Leu Ser Val Thr Ile Gly
 1               5                  10                  15

Gln Pro Ala Ser Ile Ser Cys Lys Ser Ser Gln Ser Leu Leu Asp Ser
                20                  25                  30

Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Arg Thr Phe Gly Gly Gly Thr Lys Leu Glu Ile Lys
            100                 105                 110

Arg
```

<210> SEQ ID NO 9
<211> LENGTH: 354
<212> TYPE: DNA
<213> ORGANISM: Artificial Sequence
<220> FEATURE:
<223> OTHER INFORMATION: Heavy chain coding sequence

<400> SEQUENCE: 9

```
caagttcagc tgcagcagtc tggggaggc  ttagtgaagc ctggagggtc cctgaaactc      60
tcctgtgcag cctctggatt cactttcagt gactattaca tgtattgggt tcgccagact     120
ccggaaaaga ggctggaatg ggtcgcaacc attagtgatg gtggaagtaa cacctactat     180
ccagacagtg tgaaggggcg attcaccatc tccagagaca tgccaagaa  caacctgtac     240 ctgcaaatga gcagtctgaa gtccgaggac acagccacat attactgtgc aagacgaggg     300
actgggacgg ggtttggtta ctggggccaa gggactctgg tcactgtctc tgca           354
```

<210> SEQ ID NO 10
<211> LENGTH: 321
<212> TYPE: DNA
<213> ORGANISM: Artificial Sequence
<220> FEATURE:
<223> OTHER INFORMATION: Light chain coding sequence

<400> SEQUENCE: 10

```
gacattgtgc tgacccagac tacagcctcc ctatctgttt ctgtgggaga aactgtcacc      60
```

```
atcacatgtc gagcaagtga gaatatttac agtactttag catggtatca gcagaaacag        120
ggaaaatctc ctcagctcct ggtctatgct gcaacaaact tagtagctgg tgtgccatca        180
aggttcagtg gcagtggatc aggcacacag tattccctca agatcaacag cctgcagtct        240
gaagattttg ggagttatta ctgtcaacat ttttggggta ttccgtggac gttcggtgga        300
ggcaccaagc tggaaatcaa a                                                  321

<210> SEQ ID NO 11
<211> LENGTH: 351
<212> TYPE: DNA
<213> ORGANISM: Artificial Sequence
<220> FEATURE:
<223> OTHER INFORMATION: Heavy chain coding sequence

<400> SEQUENCE: 11
gaggttcagc tgcagcagtc tggacctgag ttggtgaaac ctggggcttt agtgaagata         60
tcctgcaagg cttctggtta caccttcaca aactacgata taaactgggt gaaacagagg        120
cctggacagg gacttgagtg gattggatgg atttatcctg aagatggtag tactaagtac        180
aatgagaaat tcaagggcaa ggccacactg actgcagaca aatcctccag cacagcctac        240
atgcagctca gcagcctgac ttctgagaac tctgcagtct atttctgtgc aagagacaca        300
cgtggctact ttgactactg ggccaaggca ccactctca cagtctcctc a                  351

<210> SEQ ID NO 12
<211> LENGTH: 321
<212> TYPE: DNA
<213> ORGANISM: Artificial Sequence
<220> FEATURE:
<223> OTHER INFORMATION: Light chain coding sequence

<400> SEQUENCE: 12
gacattgtgc tcacacagtc tccagcaatc atgtctgcat ctctagggga aaggtcacc         60 atgagctgca gggccagctc aagtgtaaat tacatatact ggtaccagca gaagtcgat        120 gcctccccca aactctggat ttattacaca tccaacctgg ctcctggagt cccagctcgc       180
ttcagtggca gtgggtctgg gaactcttat tctctcacaa tcagcagcat ggagggtgaa       240
gatgctgcca cttattactg ccagcagttt actagttccc catggacgtt cggtggaggc      300
accaagctgg aattcaaacg g                                                 321

<210> SEQ ID NO 13
<211> LENGTH: 366
<212> TYPE: DNA
<213> ORGANISM: Artificial Sequence
<220> FEATURE:
<223> OTHER INFORMATION: Heavy chain coding sequence

<400> SEQUENCE: 13
caggttcagc tgcaagagtc aggacctagc cacgtgaaac cttctcagac tctgtccctc        60
acctgttctg tcactggcga ctccatcacc agtggttact ggaactggat ccggaaattc       120
ccaggaaata acttgagta tttgggggtac ataagcttca gtggtaacac ttactacaat       180
ccatctctca aaagtcgaat ctccatcatt cgagacacat ccaagaacca gtattatttg       240
cagttgaatt ctgtgactac tgaggacaca gccacatatt actgtgcaag atatccttac       300
tcctatagta actgggacta tgctatggac tactggggtc aaggaacttc agtcaccgtc       360
tcctca                                                                  366
```

<210> SEQ ID NO 14
<211> LENGTH: 339
<212> TYPE: DNA
<213> ORGANISM: Artificial Sequence
<220> FEATURE:
<223> OTHER INFORMATION: Light chain coding sequence

<400> SEQUENCE: 14

```
gatattgtga tgacacaatc tccatcctcc ctagttgtgt cagttggaga gaaggttact      60
atgagctgca agtccagtca gttccttta tatagtagca gtcaaaagaa ctacttggcc     120
tggtaccagc agaaaccagg gcagtctcct caactgctga tttactgggc atccactagg    180
gaatctgggg tccctgatcg cttcacaggc agtggatctg ggacagattt cactctcacc    240
atcagcagtg tgaaggctga agacctggca gtttattact gtcaccaata ttatagctat    300
ccgctcacgt tcggtgctgg gaccaagctg gagctgaaa                           339
```

<210> SEQ ID NO 15
<211> LENGTH: 345
<212> TYPE: DNA
<213> ORGANISM: Artificial Sequence
<220> FEATURE:
<223> OTHER INFORMATION: Heavy chain coding sequence

<400> SEQUENCE: 15

```
gaggtgaagc tggaggagtc aggacctagc ctcgtgaaac cttctcagac tctgtccctc     60
acctgttctg tctctggcga ctccatcacc attggtttct ggaactggat ccggaaattc    120
ccaggaaata aacttgagta catgggatac ataaactaca gtggtagcag ttactacaat    180
ccatctctca aaagtcgaat ctccatcact cgagacacat ccaagaacca gtattacctg    240
cagttgaatt ctgtgactcc tgaggacaca gccacatatt actgtgcaag atctgggacg    300
gaccttgact actggggcca aggcaccact ctcacagtct cctca                    345
```

<210> SEQ ID NO 16
<211> LENGTH: 339
<212> TYPE: DNA
<213> ORGANISM: Artificial Sequence
<220> FEATURE:
<223> OTHER INFORMATION: Light chain coding sequence

<400> SEQUENCE: 16

```
gatattgtgc tcacacagtc tccactcact ttgtcggtta ccattggaca accagcctcc     60
atctcttgca gtcaagtca gagcctctta gatagtgatg gaaagacata tttgaattgg    120
ttgttacaga ggccaggcca gtctccaaag cgcctaatct atctggtgtc taaactggac   180
tctggagtcc ctgacaggtt cactggcagt ggatcaggga cagatttcac actgaaaatc   240
agcagagtgg aggctgagga tttgggagtt tattattgct ggcaaggtac acattttcct   300
cggacgttcg gtggaggcac caagctggaa atcaaacgg                          339
```

<210> SEQ ID NO 17
<211> LENGTH: 200
<212> TYPE: PRT
<213> ORGANISM: Artificial Sequence
<220> FEATURE:
<223> OTHER INFORMATION: Fusion protein

<400> SEQUENCE: 17

```
Leu Ser Thr Val Thr Gly Leu His Cys Val Gly Asp Thr Tyr Pro Ser
1               5                   10                  15

Asn Asp Arg Cys Cys His Glu Cys Arg Pro Gly Asn Gly Met Val Ser
```

```
                    20                  25                  30
Arg Cys Ser Arg Ser Gln Asn Thr Val Cys Arg Pro Cys Gly Pro Gly
                35                  40                  45

Phe Tyr Asn Asp Val Val Ser Ser Lys Pro Cys Lys Pro Cys Thr Trp
        50                  55                  60

Cys Asn Leu Arg Ser Ser Glu Arg Lys Gln Leu Cys Thr Ala Thr
65                  70                  75                  80

Gln Asp Thr Val Cys Arg Cys Arg Ala Gly Thr Gln Pro Leu Asp Ser
                85                  90                  95

Tyr Lys Pro Gly Val Asp Cys Ala Pro Cys Pro Pro Gly His Phe Ser
            100                 105                 110

Pro Gly Asp Asn Gln Ala Cys Lys Pro Trp Thr Asn Cys Thr Leu Ala
            115                 120                 125

Gly Lys His Thr Leu Gln Pro Ala Ser Asn Ser Ser Asp Ala Ile Cys
            130                 135                 140

Glu Asp Arg Asp Pro Pro Ala Thr Gln Pro Gln Glu Thr Gln Gly Pro
145                 150                 155                 160

Pro Ala Arg Pro Ile Thr Val Gln Pro Thr Glu Ala Trp Pro Arg Thr
                165                 170                 175

Ser Gln Gly Pro Ser Thr Arg Pro Val Glu Val Pro Gly Gly Arg Ala
            180                 185                 190

Val Ala His His His His His His
            195                 200

<210> SEQ ID NO 18
<211> LENGTH: 8
<212> TYPE: PRT
<213> ORGANISM: Artificial Sequence
<220> FEATURE:
<223> OTHER INFORMATION: CDRH1

<400> SEQUENCE: 18

Gly Phe Thr Phe Ser Asp Tyr Tyr
1               5

<210> SEQ ID NO 19
<211> LENGTH: 8
<212> TYPE: PRT
<213> ORGANISM: Artificial Sequence
<220> FEATURE:
<223> OTHER INFORMATION: CDRH2

<400> SEQUENCE: 19

Ile Ser Asp Gly Gly Ser Asn Thr
1               5

<210> SEQ ID NO 20
<211> LENGTH: 11
<212> TYPE: PRT
<213> ORGANISM: Artificial Sequence
<220> FEATURE:
<223> OTHER INFORMATION: CDRH3

<400> SEQUENCE: 20

Ala Arg Arg Gly Thr Gly Thr Gly Phe Gly Tyr
1               5                   10

<210> SEQ ID NO 21
<211> LENGTH: 6
<212> TYPE: PRT
<213> ORGANISM: Artificial Sequence
```

```
<220> FEATURE:
<223> OTHER INFORMATION: CDRL1

<400> SEQUENCE: 21

Glu Asn Ile Tyr Ser Thr
1               5

<210> SEQ ID NO 22
<211> LENGTH: 9
<212> TYPE: PRT
<213> ORGANISM: Artificial Sequence
<220> FEATURE:
<223> OTHER INFORMATION: CDRL3

<400> SEQUENCE: 22

Gln His Phe Trp Gly Ile Pro Trp Thr
1               5

<210> SEQ ID NO 23
<211> LENGTH: 8
<212> TYPE: PRT
<213> ORGANISM: Artificial Sequence
<220> FEATURE:
<223> OTHER INFORMATION: CDRH1

<400> SEQUENCE: 23

Gly Tyr Thr Phe Thr Asn Tyr Asp
1               5

<210> SEQ ID NO 24
<211> LENGTH: 8
<212> TYPE: PRT
<213> ORGANISM: Artificial Sequence
<220> FEATURE:
<223> OTHER INFORMATION: CDRH2

<400> SEQUENCE: 24

Ile Tyr Pro Glu Asp Gly Ser Thr
1               5

<210> SEQ ID NO 25
<211> LENGTH: 10
<212> TYPE: PRT
<213> ORGANISM: Artificial Sequence
<220> FEATURE:
<223> OTHER INFORMATION: CDRH3

<400> SEQUENCE: 25

Ala Arg Asp Thr Arg Gly Tyr Phe Asp Tyr
1               5                   10

<210> SEQ ID NO 26
<211> LENGTH: 5
<212> TYPE: PRT
<213> ORGANISM: Artificial Sequence
<220> FEATURE:
<223> OTHER INFORMATION: CDRL1

<400> SEQUENCE: 26

Ser Ser Val Asn Tyr
1               5

<210> SEQ ID NO 27
<211> LENGTH: 9
<212> TYPE: PRT
<213> ORGANISM: Artificial Sequence
<220> FEATURE:
```

```
<223> OTHER INFORMATION: CDRL3

<400> SEQUENCE: 27

Gln Gln Phe Thr Ser Ser Pro Trp Thr
1               5

<210> SEQ ID NO 28
<211> LENGTH: 8
<212> TYPE: PRT
<213> ORGANISM: Artificial Sequence
<220> FEATURE:
<223> OTHER INFORMATION: CDRH1

<400> SEQUENCE: 28

Gly Asp Ser Ile Thr Ser Gly Tyr
1               5

<210> SEQ ID NO 29
<211> LENGTH: 7
<212> TYPE: PRT
<213> ORGANISM: Artificial Sequence
<220> FEATURE:
<223> OTHER INFORMATION: CDRH2

<400> SEQUENCE: 29

Ile Ser Phe Ser Gly Asn Thr
1               5

<210> SEQ ID NO 30
<211> LENGTH: 16
<212> TYPE: PRT
<213> ORGANISM: Artificial Sequence
<220> FEATURE:
<223> OTHER INFORMATION: CDRH3

<400> SEQUENCE: 30

Ala Arg Tyr Pro Tyr Ser Tyr Ser Asn Trp Asp Tyr Ala Met Asp Tyr
1               5                   10                  15

<210> SEQ ID NO 31
<211> LENGTH: 12
<212> TYPE: PRT
<213> ORGANISM: Artificial Sequence
<220> FEATURE:
<223> OTHER INFORMATION: CDRL1

<400> SEQUENCE: 31

Gln Phe Leu Leu Tyr Ser Ser Ser Gln Lys Asn Tyr
1               5                   10

<210> SEQ ID NO 32
<211> LENGTH: 9
<212> TYPE: PRT
<213> ORGANISM: Artificial Sequence
<220> FEATURE:
<223> OTHER INFORMATION: CDRL3

<400> SEQUENCE: 32

His Gln Tyr Tyr Ser Tyr Pro Leu Thr
1               5

<210> SEQ ID NO 33
<211> LENGTH: 8
<212> TYPE: PRT
<213> ORGANISM: Artificial Sequence
<220> FEATURE:
<223> OTHER INFORMATION: CDRH1
```

```
<400> SEQUENCE: 33

Gly Asp Ser Ile Thr Ile Gly Phe
1               5

<210> SEQ ID NO 34
<211> LENGTH: 7
<212> TYPE: PRT
<213> ORGANISM: Artificial Sequence
<220> FEATURE:
<223> OTHER INFORMATION: CDRH2

<400> SEQUENCE: 34

Ile Asn Tyr Ser Gly Ser Ser
1               5

<210> SEQ ID NO 35
<211> LENGTH: 9
<212> TYPE: PRT
<213> ORGANISM: Artificial Sequence
<220> FEATURE:
<223> OTHER INFORMATION: CDRH3

<400> SEQUENCE: 35

Ala Arg Ser Gly Thr Asp Leu Asp Tyr
1               5

<210> SEQ ID NO 36
<211> LENGTH: 11
<212> TYPE: PRT
<213> ORGANISM: Artificial Sequence
<220> FEATURE:
<223> OTHER INFORMATION: CDRL1

<400> SEQUENCE: 36

Gln Ser Leu Leu Asp Ser Asp Gly Lys Thr Tyr
1               5                   10

<210> SEQ ID NO 37
<211> LENGTH: 9
<212> TYPE: PRT
<213> ORGANISM: Artificial Sequence
<220> FEATURE:
<223> OTHER INFORMATION: CDRL3

<400> SEQUENCE: 37

Trp Gln Gly Thr His Phe Pro Arg Thr
1               5
```

ANTI-OX40 MONOCLONAL ANTIBODY AND APPLICATION THEREOF

CROSS-REFERENCE TO RELATED APPLICATIONS

This application is a U.S. National Phase Application based on International Application No. PCT/CN2018/123393 filed on Dec. 25, 2018, the entire contents of which is incorporated by reference herein.

FIELD

The present disclosure relates to the field of biomedicine. More specifically, the present disclosure relates to an anti-OX40 monoclonal antibody and use thereof.

BACKGROUND

OX40, also known as CD134 and TNFRSF4, is a member of the tumor necrosis factor receptor (TNFR) superfamily, and only expressed on the surface of activated CD4+ T cells and CD8+ T cells. Human OX40 is a type I transmembrane glycoprotein with a molecular mass of 47-51 kDa, composed of 249 amino acids, in which the extramembrane, transmembrane, and intramembrane regions are composed of 188, 24, and 37 amino acids, respectively. The corresponding gene is located in Human chromosome 1p36. OX40 signal can activate the downstream NF-kB, PI3K and PKB pathways, and the continuous activation of these pathways can ultimately prolong the survival time of T cells, expand T cell memory, and promote the cell killing ability of T cells. In addition, OX40 can also improve the immunosuppressive effect in the tumor microenvironment by inhibiting the differentiation and activity of regulatory T cells (Treg), further enhancing the function of effector T cells.

OX40 as a target for treatment needs further improvement.

SUMMARY

The present disclosure aims to solve one of the technical problems in the related art at least to a certain extent. To this end, an object of the present disclosure is to provide an anti-OX40 monoclonal antibody. The OX40 antibody provided by the present disclosure can be used to enhance immune response to treat cancer and infectious disease, or as an adjuvant for cancer vaccines.

According to a first aspect of the present disclosure, the present disclosure provides an anti-OX40 antibody or antigen-binding fragment thereof, comprising at least one of: (1) a heavy chain variable region comprising amino acid sequences of GFTFSDYY (SEQ ID NO: 18), ISDGGSNT (SEQ ID NO: 19) and ARRGTGTGFGY (SEQ ID NO: 20), and a light chain variable region comprising amino acid sequences of ENIYST (SEQ ID NO: 21), AAT and QHFWGIPWT (SEQ ID NO: 22); (2) a heavy chain variable region comprising amino acid sequences of GYTFTNYD (SEQ ID NO: 23), IYPEDGST (SEQ ID NO: 24) and ARDTRGYFDY (SEQ ID NO: 25), and a light chain variable region comprising amino acid sequences of SSVNY (SEQ ID NO: 26), YTS and QQFTSSPWT (SEQ ID NO: 27); (3) a heavy chain variable region comprising amino acid sequences of GDSITSGY (SEQ ID NO: 28), ISFSGNT (SEQ ID NO: 29) and ARYPYSYSNWDYAMDY (SEQ ID NO: 30), and a light chain variable region comprising amino acid sequences of QFLLYSSSQKNY (SEQ ID NO: 31), WAS and HQYYSYPLT (SEQ ID NO: 32); (4) a heavy chain variable region comprising amino acid sequences of GDSITIGF (SEQ ID NO: 33), INYSGSS (SEQ ID NO: 34) and ARSGTDLDY (SEQ ID NO: 35), and a light chain variable region comprising amino acid sequences of QSLLDSDGKTY (SEQ ID NO: 36), LVS and WQGTHFPRT (SEQ ID NO: 37); (5) an amino acid sequence of any of (1) to (4) with one or more conservative amino acid mutations.

According to an embodiment of the present disclosure, the amino acid sequence of any of (1) to (4) with one or more conservative amino acid mutations is preferably an amino acid sequence with one conservative amino acid mutation, an amino acid sequence with two conservative amino acid mutations, or an amino acid sequence with three conservative amino acid mutations.

According to an embodiment of the present disclosure, the antibody or antigen-binding fragment thereof may further comprise: (a) a heavy chain comprising the amino acid sequence shown in SEQ ID NO: 1 and a light chain comprising the amino acid sequence shown in SEQ ID NO: 2; (b) a heavy chain comprising the amino acid sequence shown in SEQ ID NO: 3 and a light chain comprising the amino acid sequence shown in SEQ ID NO: 4; (c) a heavy chain comprising the amino acid sequence shown in SEQ ID NO: 5 and a light chain comprising the amino acid sequence shown in SEQ ID NO: 6; (d) a heavy chain comprising the amino acid sequence shown in SEQ ID NO: 7 and a light chain comprising the amino acid sequence shown in SEQ ID NO: 8; (e) any of (a) to (d) with one or more conservative amino acid mutations in the amino acid sequence region other than the heavy chain variable region and the light chain variable region. According to an embodiment of the present disclosure, any of (a) to (d) with one or more conservative amino acid mutations in the amino acid sequence region other than the heavy chain variable region and the light chain variable region may have one conservative amino acid mutation, two conservative amino acid mutations or three conservative amino acid mutations.

According to an embodiment of the present disclosure, the antibody is a monoclonal antibody.

According to a second aspect of the present disclosure, the present disclosure provides an isolated polynucleotide encoding the antibody or antigen-binding fragment thereof according to the first aspect of the present disclosure.

According to an embodiment of the present disclosure, the polynucleotide has at least one of: an nucleotide sequence shown in SEQ ID NO: 9 and an nucleotide sequence shown in SEQ ID NO: 10; an nucleotide sequence shown in SEQ ID NO: 11 and an nucleotide sequence shown in SEQ ID NO: 12; an nucleotide sequence shown in SEQ ID NO: 13 and an nucleotide sequence shown in SEQ ID NO: 14; an nucleotide sequence shown in SEQ ID NO: 15 and an nucleotide sequence shown in SEQ ID NO: 16.

According to a third aspect of the present disclosure, the present disclosure provides an expression vector comprising the polynucleotide according to the second aspect of the present disclosure. The expression vector comprises the polynucleotide, and the expression vector may be a plasmid, for example, a circular double-stranded DNA into which the polynucleotide may be inserted; the expression vector may also be a viral vector, and the polynucleotide may be inserted into the viral genome. Certain expression vectors may be introduced into a host cell to replicate autonomously, and certain expression vectors may be integrated into the genome of the host cell when introduced into the host cell, thereby replicating together with the host genome.

According to an embodiment of the present disclosure, the above-mentioned expression vector may further have the following technical features:

In some embodiments of the present disclosure, the expression vector further comprises: a control element operably linked to the polynucleotide for controlling the expression of the polynucleotide in the host cell. "Operably linked" refers to linking a foreign gene to a vector so that the control elements in the vector, such as transcription control sequence and translation control sequence, may perform their expected functions of regulating the transcription and translation of the foreign gene. Of course, the polynucleotides encoding the light chain and heavy chain of an antibody may be inserted into different vectors independently, and more commonly, inserted into the same vector.

In some embodiments of the present disclosure, the control element includes at least one of: a promoter, an enhancer, and a terminator.

In some embodiments of the present disclosure, the host cell is a mammalian cell.

According to a fourth aspect of the present disclosure, the present disclosure provides a recombinant cell comprising the expression vector according to any of the embodiments of the third aspect of the present disclosure. Herein, the recombinant cell refers to a cell into which an expression vector has been introduced. It should be understood that the recombinant cell not only refers to a cell of a specific object, but also refers to a progeny cell of such cell. Some changes may occur in subsequent passages due to mutations or environmental influences, so such progeny cells may not be exactly the same as the parent cells, however, they are still included in the scope of the recombinant cells referred to herein.

According to a fifth aspect of the present disclosure, the present disclosure provides a method for preparing the antibody or antigen-binding fragment thereof according to any of the embodiments of the first aspect of the present disclosure. The method includes culturing the recombinant cell according to the fourth aspect of the present disclosure.

According to a sixth aspect of the present disclosure, the present disclosure provides use of a polynucleotide, an expression vector, or a recombinant cell in the preparation of an antibody or antigen-binding fragments thereof, which specifically binds to OX40. According to an embodiment of the present disclosure, the polynucleotide is the polynucleotide according to the second aspect of the present disclosure, the expression vector is the expression vector according to the third aspect of the present disclosure, and the recombinant cell is the recombinant cell according to the fourth aspect of the present disclosure.

According to a seventh aspect of the present disclosure, the present disclosure provides a hybridoma cell, at least one selected from: hybridoma cell HX011-9C12, deposited in the China Center for Type Culture Collection on Sep. 27, 2018 with a deposit number C2018197; hybridoma cell HX011-1D9, deposited in the China Center for Type Culture Collection. on Sep. 27, 2018 with a deposit number C2018198. The address of China Center for Type Culture Collection is 30072, Wuhan University, No. 299 Bayi Road, Wuchang District, Wuhan City, Hubei Province, China. The deposit was made under conditions that are consistent with those specified in the rules of the Budapest Treaty, including the provision that requires, with one possible exception (37 CFR 1.808(b)), and that all restrictions on the accessibility be irrevocably removed by the applicant upon the granting of the patent.

According to an eighth aspect of the present disclosure, the present disclosure provides use of a hybridoma cell in the preparation of a monoclonal antibody against OX40, wherein the hybridoma cell is the hybridoma cell according to the seventh aspect of the present disclosure.

According to a ninth aspect of the present disclosure, the present disclosure provides use of an antibody or antigen-binding fragment thereof, a polynucleotide, an expression vector, a recombinant cell or a hybridoma cell in the preparation of a medicament for the treatment of autoimmune disease or cancer. The medicament may be used to inhibit the growth of tumor cells, including but not limited to in breast cancer, prostate cancer, colorectal cancer or B-cell lymphoma cells. Moreover, the medicament may also be used to treat an autoimmune disease, including but not limited to rheumatoid arthritis, multiple sclerosis, diabetes, Crohn's disease, inflammatory bowel disease, ulcerative colitis, Celiac disease, psoriasis, proliferative lupus nephritis, granulomatous myopathy and polymyositis.

According to an embodiment of the present disclosure, the antibody or antigen-binding fragment thereof is the antibody or antigen-binding fragment thereof according to the first aspect of the present disclosure, the polynucleotide is the polynucleotide according to the second aspect of the present disclosure, the expression vector is the expression vector according to the third aspect of the present disclosure, the recombinant cell is the recombinant cell according to the fourth aspect of the present disclosure, and the hybridoma cell is the hybridoma cell according to the seventh aspect of the present disclosure.

According to a tenth aspect of the present disclosure, the present disclosure provides a pharmaceutical composition comprising an antibody or antigen-binding fragment thereof, a polynucleotide, an expression vector, a recombinant cell or a hybridoma cell. According to an embodiment of the present disclosure, the antibody or antigen-binding fragment thereof is the antibody or antigen-binding fragment thereof according to the first aspect of the present disclosure, the polynucleotide is the polynucleotide according to the second aspect of the present disclosure, the expression vector is the expression vector according to the third aspect of the present disclosure, the recombinant cell is the recombinant cell according to the fourth aspect of the present disclosure, and the hybridoma cell is the hybridoma according to the seventh aspect of the present disclosure cell.

The anti-OX40 antibodies provided herein can be incorporated into a pharmaceutical composition suitable for administration to a subject. Generally, these pharmaceutical compositions comprise the anti-OX40 antibody provided herein and a pharmaceutically acceptable carrier. The "pharmaceutically acceptable carrier" may include any and all solvents, dispersion media, coatings, antibacterial and antifungal agents, isotonic and absorption delaying agents, and the like that are physiologically compatible. Specific examples may be one or more of water, saline, phosphate buffered saline, glucose, glycerol, ethanol and combinations thereof. In many cases, the pharmaceutical composition includes isotonic agents, such as sugars, polyalcohols (such as mannitol, sorbitol), or sodium chloride. Of course, the pharmaceutically acceptable carrier may also include minor amounts of auxiliary substances, such as wetting or emulsifying agents, preservatives or buffers, to extend the shelf life or efficacy of the antibody.

For example, the antibodies of the present disclosure may be incorporated into a pharmaceutical composition suitable for parenteral administration (e.g., intravenous, subcutaneous, intraperitoneal, intramuscular). These pharmaceutical composition may be prepared in various forms, for example, liquid, semi-solid and solid dosage forms, including but not limited to liquid solutions (for example, injection solutions and infusion solutions), dispersions or suspensions, tablets, pills, powders, liposomes, and suppositories. Typical pharmaceutical compositions are in the form of injection solutions or infusion solutions. The antibody may be administered by intravenous infusion or injection, or intramuscular or subcutaneous injection.

According to an eleventh aspect of the present disclosure, the present disclosure provides a method for identifying a drug capable of binding to OX40, comprising: contacting an antibody or antigen-binding fragment thereof described in any of the embodiments of the first aspect of the present disclosure with an antigen in the presence of a candidate drug, and determining a first binding amount of the antibody or antigen-binding fragment thereof to the antigen; and contacting the antibody or antigen-binding fragment thereof described in any of the embodiments of the first aspect of the present disclosure with the candidate drug in the absence of the candidate drug, and determining a second binding amount of the antibody or antigen-binding fragment thereof to the antigen; wherein the antigen is OX40 or fragment thereof, and the second binding amount greater than the first binding amount indicates that the candidate drug is capable of binding to OX40. The binding amount of the antibody with the antigen in the absence of the candidate drug is determined, and then after adding the candidate drug, the binding amount of the antibody with the antigen is determined again, and then the difference between the two determined binding amounts is determined. Reduced binding amount of the antibody with the antigen after the addition of the candidate drug indicates that the candidate drug can competitively bind to the OX40 antigen, so that a drug that is capable of binding to OX40 can be identified.

According to a twelfth aspect of the present disclosure, the present disclosure provides a drug combination comprising: (1) an antibody or antigen-binding fragment thereof, a polynucleotide, an expression vector, a recombinant cell or a hybridoma cell; and (2) an immune enhancing agent other than (1), wherein the antibody or antigen-binding fragment thereof is the antibody or antigen-binding fragment thereof according to the first aspect of the present disclosure, the polynucleotide is the polynucleotide according to the second aspect of the present disclosure, the expression vector is the expression vector according to the third aspect of the present disclosure, the recombinant cell is the recombinant cell according to the fourth aspect of the present disclosure, and the hybridoma cell is the hybridoma according to the seventh aspect of the present disclosure cell.

According to an embodiment of the present disclosure, the immune enhancing agent other than (1) is at least one selected from: an anti-PD1 antibody, LAG-3 antibody, CTLA-4 antibody, Tim3 antibody or PD-L1 antibody. These immune enhancing agents may bind to specific targets. Through the combination or combined use of these immune enhancing agents and anti-OX40 antibodies, the combination therapy can exert therapeutic effects at lower doses.

According to a thirteenth aspect of the present disclosure, the present disclosure provides a method for treating cancer, comprising administering the antibody or antigen-binding fragment thereof according to any of the first aspect of the present disclosure to a subject in need.

According to an embodiment of the present disclosure, in the method for treating cancer described above, the cancer is selected from breast cancer, prostate cancer, ovarian cancer, colorectal cancer or B-cell lymphoma.

BRIEF DESCRIPTION OF THE DRAWINGS

The above and/or additional aspects and advantages of the present disclosure will become obvious and easy to understand from the description of the embodiments in conjunction with the following drawings, in which.

BIOLOGICAL PRESERVATION

Figure 1:
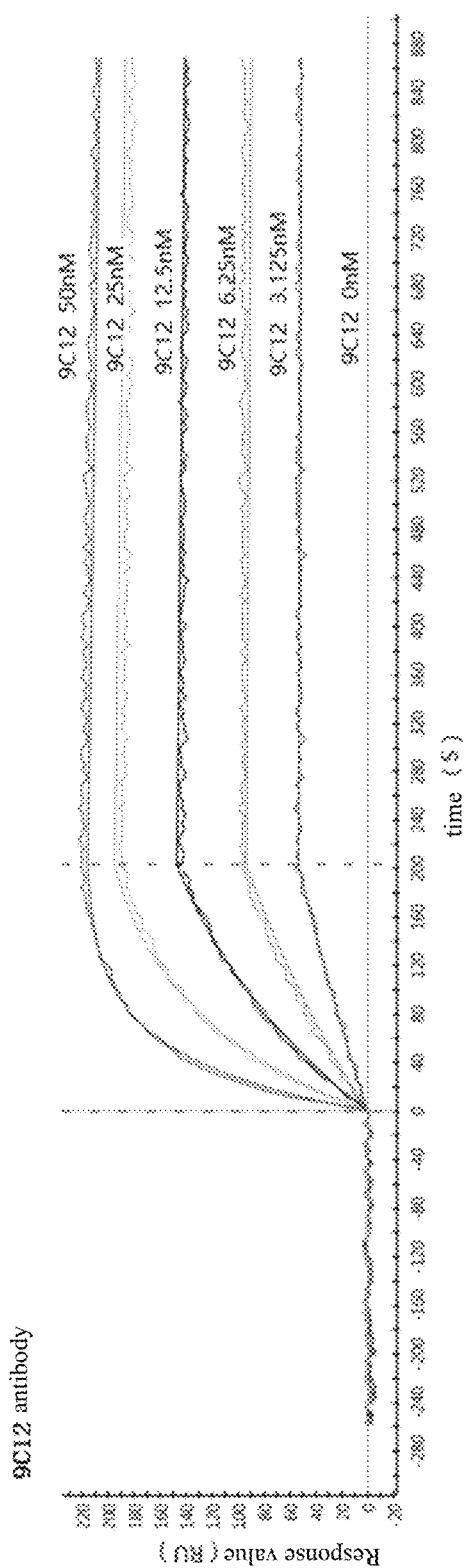
FIG. 1 is a graph showing the kinetic parameters of the 9C12 antibody according to an embodiment of the present disclosure.

Hybridoma cell HX011-9C12, was deposited in the China Center for Type Culture Collection at Wuhan University, Wuhan, China, with a deposit number C2018197, on Sep. 27, 2018.

Hybridoma cell HX011-1D9, was deposited in the China Center for Type Culture Collection at Wuhan University, Wuhan, China, with a deposit number C2018198, on Sep. 27, 2018.

DETAILED DESCRIPTION

The embodiments of the present disclosure are described in detail below. Examples of the embodiments are shown in the accompanying drawings, in which the same or similar reference numerals indicate the same or similar elements or elements with the same or similar functions. The embodiments described below with reference to the accompanying drawings are exemplary, and are intended to explain the present disclosure, but should not be construed as limiting the present disclosure.

In order to improve the therapeutic effect of OX40 as a target, the present disclosure provides an anti-OX40 antibody and the use of the antibody in drug therapy. The anti-OX40 antibody provided by the present disclosure may be used to treat autoimmune disease or cancer. Herein, the anti-OX40 antibody may also be expressed as an OX40 antibody or as an isolated anti-OX40 antibody as required.

As used herein, the term "monoclonal antibody" refers to antibodies obtained from a population of substantially homologous antibodies, including, but not limited to, monoclonal antibodies prepared by hybridoma or recombinant DNA methods. "Anti-OX40 antibody" is sometimes referred to as "OX40 antibody" herein.

Herein, the term "antibody" is an immunoglobulin molecule composed of four polypeptide chains, two heavy chains and two light chains internally linked by disulfide bonds. Each heavy chain is composed of a heavy chain variable region and a heavy chain constant region. Each light chain is composed of a light chain variable region and a light chain constant region. The heavy chain variable region and the light chain variable region may further include a complementarity determining region, also called a hypervariable region (CDR).

The term "antigen-binding fragment" of an antibody includes antibody fragments that retain the ability to specifically bind to an antigen (hOX40).

Specifically, the cancer described herein may be lung cancer, prostate cancer, breast cancer, head and neck cancer, esophageal cancer, stomach cancer, colon cancer, colorectal cancer, bladder cancer, cervical cancer, uterine cancer, ovarian cancer, liver cancer, blood system cancer, or any other disease or condition characterized by uncontrolled cell growth.

Herein, the autoimmune disease may be rheumatoid arthritis, multiple sclerosis, diabetes, Crohn's disease, inflammatory bowel disease, ulcerative colitis, celiac disease, psoriasis, proliferative lupus nephritis, granulomatous myopathy and polymyositis, etc.

According to an aspect of the present disclosure, the present disclosure provides an anti-OX40 antibody or antigen-binding fragment thereof, comprising at least one of: (1) a heavy chain variable region comprising amino acid sequences of GFTFSDYY (SEQ ID NO: 18), ISDGGSNT (SEQ ID NO: 19) and ARRGTGTGFGY (SEQ ID NO: 20), and a light chain variable region comprising amino acid sequences of ENIYST (SEQ ID NO: 21), AAT and QHFWGIPWT (SEQ ID NO: 22); (2) a heavy chain variable region comprising amino acid sequences of GYTFTNYD (SEQ ID NO: 23), IYPEDGST (SEQ ID NO: 24) and ARDTRGYFDY (SEQ ID NO: 25), and a light chain variable region comprising amino acid sequences of SSVNY (SEQ ID NO: 26), YTS and QQFTSSPWT (SEQ ID NO: 27); (3) a heavy chain variable region comprising amino acid sequences of GDSITSGY (SEQ ID NO: 28), ISFSGNT (SEQ ID NO: 29) and ARYPYSYSNWDYAMDY (SEQ ID NO: 30), and a light chain variable region comprising amino acid sequences of QFLLYSSSQKNY (SEQ ID NO: 31), WAS and HQYYSYPLT (SEQ ID NO: 32);(4) a heavy chain variable region comprising amino acid sequences of GDSITIGF (SEQ ID NO: 33), INYSGSS (SEQ ID NO: 34) and ARSGTDLDY (SEQ ID NO: 35), and a light chain variable region comprising amino acid sequences of QSLLDSDGKTY (SEQ ID NO: 36), LVS and WQGTHFPRT (SEQ ID NO: 37); (5) an amino acid sequence of any of (1) to (4) with one or more conservative amino acid substitutions.

The "conservative amino acid substitution" refers to the substitution of an amino acid for another amino acid with biological, chemical or structural similarity. Biological similarity means that the substitution does not destroy the biological activity of OX40. Structural similarity means amino acids having side chains of similar length, such as alanine, glycine, or serine, or amino acids having side chains of similar size. Chemical similarity means amino acids having the same charge or hydrophilic or hydrophobic properties. For example, the hydrophobic residues isoleucine, valine, leucine or methionine may be substituted for each other. Alternatively, polar amino acids such as arginine may be substituted for lysine, glutamic acid for aspartic acid, glutamine for asparagine, serine for threonine and so on.

According to an embodiment of the present disclosure, the present disclosure provides an anti-OX40 antibody, in which the heavy chain variable region has three hypervariable regions containing the following amino acid sequences determined according to the IMGT numbering system: CDRH1 (GFTFSDYY, SEQ ID NO: 18), CDRH2 (ISDGGSNT, SEQ ID NO: 19), CDRH3 (ARRGTGTGFGY, SEQ ID NO: 20); and the light chain variable region has three hypervariable regions containing the following amino acid sequences determined according to the IMGT numbering system: CDRL1 (ENIYST, SEQ ID NO: 21), CDRL2 (AAT), CDRL3 (QHFWGIPWT, SEQ ID NO: 22).

In a specific embodiment of the present disclosure, the antibody is 9C12, with a heavy chain amino acid sequence (SEQ ID NO:1):

Q V Q L Q Q S G G G L V K P G G S L K L S C A A S
G F T F S D Y Y M Y W V R Q T P E K R L E W V A T
I S D G G S N T Y Y P D S V K G R F T I S R D N A
K N N L Y L Q M S S L K S E D T A T Y Y C <u>A R R G</u>
<u>T G T G F G Y</u> W G Q G T L V T V S A;

and a light chain amino acid sequence (SEQ ID NO:2):

D I V L T Q T T A S L S V S V G E T V T I T C R A
S <u>E N I Y S T</u> L A W Y Q Q K Q G K S P Q L L V Y <u>A</u>
<u>A T</u> N L V A G V P S R F S G S G S G T Q Y S L K I
N S L Q S E D F G S Y Y C <u>Q H F W G I P W T</u> F G G
G T K L E I K.

The sequences of the hypervariable regions on the heavy and light chains of the antibody determined according to the IMGT numbering system are underlined.

According to a specific embodiment of the present disclosure, the heavy chain amino acid sequence shown in SEQ ID NO: 1 is encoded by the nucleotide sequence (SEQ ID NO: 9):

CAAGTTCAGCTGCAGCAGTCTGGGGGAGGCTTAGTGAAGCCTGGAGGGTC

CCTGAAACTCTCCTGTGCAGCCTCTGGATTCACTTTCAGTGACTATTACA

TGTATTGGGTTCGCCAGACTCCGGAAAAGAGGCTGGAATGGGTCGCAACC

ATTAGTGATGGTGGAAGTAACACCTACTATCCAGACAGTGTGAAGGGGCG

ATTCACCATCTCCAGAGACAATGCCAAGAACAACCTGTACCTGCAAATGA

GCAGTCTGAAGTCCGAGGACACAGCCACATATTACTGTGCAAGACGAGGG

ACTGGGACGGGGTTTGGTTACTGGGGCCAAGGGACTCTGGTCACTGTCTC

TGCA.

According to a specific embodiment of the present disclosure, the light chain amino acid sequence shown in SEQ ID NO: 2 is encoded by the nucleotide sequence (SEQ ID NO: 10):

GACATTGTGCTGACCCAGACTACAGCCTCCCTATCTGTTTCTGTGGGAGA

AACTGTCACCATCACATGTCGAGCAAGTGAGAATATTTACAGTACTTTAG

CATGGTATCAGCAGAAACAGGGAAAATCTCCTCAGCTCCTGGTCTATGCT

GCAACAAACTTAGTAGCTGGTGTGCCATCAAGGTTCAGTGGCAGTGGATC

```
AGGCACACAGTATTCCCTCAAGATCAACAGCCTGCAGTCTGAAGATTTTG

GGAGTTATTACTGTCAACATTTTTGGGGTATTCCGTGGACGTTCGGTGGA

GGCACCAAGCTGGAAATCAAA.
```

According to an embodiments of the present disclosure, the present disclosure provides yet another anti-OX40 antibody, in which the heavy chain variable region has three hypervariable regions containing the following amino acid sequences determined according to the IMGT numbering system: CDRH1 (GYTFTNYD, SEQ ID NO: 23), CDRH2 (IYPEDGST, SEQ ID NO: 24), CDRH3 (ARDTRGYFDY, SEQ ID NO: 25); and the light chain variable region has three hypervariable regions containing the following amino acid sequences determined according to the IMGT numbering system: CDRL1 (SSVNY, SEQ ID NO: 26), CDRL2 (YTS), CDRL3 (QQFTSSPWT, SEQ ID NO: 27).

In a specific embodiment of the present disclosure, the antibody is 1D9, with a heavy chain amino acid sequence (SEQ ID NO:3)

```
E V Q L Q Q S G P E L V K P G A L V K I S C K A S

G Y T F T N Y D I N W V K Q R P G Q G L E W I G W

I Y P E D G S T K Y N E K F K G K A T L T A D K S

S S T A Y M Q L S S L T S E N S A V Y F C A R D T

R G Y F D Y W G Q G T T L T V S S;
``` and a light chain amino acid sequence (SEQ ID NO:4):

```
D I V M T Q T T A I M S A S L G E K V T M S C R A

S S S V N Y I Y W Y Q Q K S D A S P K L W I Y Y T

S N L A P G V P A R F S G S G S G N S Y S L T I S

S M E G E D A A T Y Y C Q Q F T S S P W T F G G G

T K L E F K R.
```

The sequences of the hypervariable regions on the heavy and light chains of the antibody determined according to the IMGT numbering system are underlined.

According to an embodiment of the present disclosure, the heavy chain amino acid sequence shown in SEQ ID NO: 3 is encoded by the nucleotide sequence (SEQ ID NO: 11):

```
GAGGTTCAGCTGCAGCAGTCTGGACCTGAGTTGGTGAAACCTGGGGCTTT

AGTGAAGATATCCTGCAAGGCTTCTGGTTACACCTTCACAAACTACGATA

TAAACTGGGTGAAACAGAGGCCTGGACAGGGACTTGAGTGGATTGGATGG

ATTTATCCTGAAGATGGTAGTACTAAGTACAATGAGAAATTCAAGGGCAA

GGCCACACTGACTGCAGACAAATCCTCCAGCACAGCCTACATGCAGCTCA

GCAGCCTGACTTCTGAGAACTCTGCAGTCTATTTCTGTGCAAGAGACACA

CGTGGCTACTTTGACTACTGGGGCCAAGGCACCACTCTCACAGTCTCCTC

A.
```

According to a specific embodiment of the present disclosure, the light chain amino acid sequence shown in SEQ ID NO: 4 is encoded by the nucleotide sequence (SEQ ID NO: 12):

```
GACATTGTGCTCACACAGTCTCCAGCAATCATGTCTGCATCTCTAGGGGA

GAAGGTCACCATGAGCTGCAGGGCCAGCTCAAGTGTAAATTACATATACT

GGTACCAGCAGAAGTCAGATGCCTCCCCCAAACTCTGGATTTATTACACA

TCCAACCTGGCTCCTGGAGTCCCAGCTCGCTTCAGTGGCAGTGGGTCTGG

GAACTCTTATTCTCTCACAATCAGCAGCATGGAGGGTGAAGATGCTGCCA

CTTATTACTGCCAGCAGTTTACTAGTTCCCCATGGACGTTCGGTGGAGGC

ACCAAGCTGGAATTCAAACGG.
```

According to an embodiment of the present disclosure, the present disclosure provides another anti-OX40 antibody, in which the heavy chain variable region has three hypervariable regions containing the following amino acid sequences determined according to the IMGT numbering system: CDRH1 (GDSITSGY, SEQ ID NO: 28), CDRH2 (ISFSGNT, SEQ ID NO: 29), CDRH3 (ARYPYSYS-NWDYAMDY, SEQ ID NO: 30)); and the light chain variable region has three hypervariable regions containing the following amino acid sequences determined according to the IMGT numbering system: CDRL1 (QFLLYSSSQKNY, SEQ ID NO: 31), CDRL2 (WAS), CDRL3 (HQYYSYPLT, SEQ ID NO: 32).

In a specific embodiment of the present disclosure, the antibody is 8A7, with a heavy chain amino acid sequence (SEQ ID NO:5)

```
Q V Q L Q E S G P S H V K P S Q T L S L T C S V T

G D S I T S G Y W N W I R K F P G N K L E Y L G Y

I S F S G N T Y Y N P S L K S R I S I I R D T S K

N Q Y Y L Q L N S V T T E D T A T Y Y C A R Y P Y

S Y S N W D Y A M D Y W G Q G T S V T V S S;
``` and a light chain amino acid sequence (SEQ ID NO:6):

```
    D I V M T Q S P S S L V V

S V G E K V T M S C K S S Q F L L Y S S S Q

K N Y L A W Y Q Q K P G Q S P Q L L I Y W A

S T R E S G V P D R F T G S G S G T D F T L

T I S S V K A E D L A V Y Y C H Q Y Y S Y P

L T F G A G T K L E L K.
```

The sequences of the hypervariable regions on the heavy and light chains of the antibody determined according to the IMGT numbering system are underlined.

According to a specific embodiment of the present disclosure, the heavy chain amino acid sequence shown in SEQ ID NO: 5 is encoded by the nucleotide sequence (SEQ ID NO: 13):

```
CAGGTTCAGCTGCAAGAGTCAGGACCTAGCCACGTGAAACCTTCTCAGAC

TCTGTCCCTCACCTGTTCTGTCACTGGCGACTCCATCACCAGTGGTTACT

GGAACTGGATCCGGAAATTCCCAGGAAATAAACTTGAGTATTTGGGGTAC

ATAAGCTTCAGTGGTAACACTTACTACAATCCATCTCTCAAAAGTCGAAT
```

```
CTCCATCATTCGAGACACATCCAAGAACCAGTATTATTTGCAGTTGAATT

CTGTGACTACTGAGGACACAGCCACATATTACTGTGCAAGATATCCTTAC

TCCTATAGTAACTGGGACTATGCTATGGACTACTGGGGTCAAGGAACTTC

AGTCACCGTCTCCTCA.
```

According to a specific embodiment of the present disclosure, the light chain amino acid sequence shown in SEQ ID NO: 6 is encoded by the nucleotide sequence (SEQ ID NO: 14):

```
GATATTGTGATGACACAATCTCCATCCTCCCTAGTTGTGTCAGTTGGAGA

GAAGGTTACTATGAGCTGCAAGTCCAGTCAGTTCCTTTTATATAGTAGCA

GTCAAAAGAACTACTTGGCCTGGTACCAGCAGAAACCAGGGCAGTCTCCT

CAACTGCTGATTTACTGGGCATCCACTAGGGAATCTGGGGTCCCTGATCG

CTTCACAGGCAGTGGATCTGGGACAGATTTCACTCTCACCATCAGCAGTG

TGAAGGCTGAAGACCTGGCAGTTTATTACTGTCACCAATATTATAGCTAT

CCGCTCACGTTCGGTGCTGGGACCAAGCTGGAGCTGAAA.
```

According to the embodiments of the present disclosure, the present disclosure provides yet another anti-OX40 antibody, in which the heavy chain variable region has three hypervariable regions containing the following amino acid sequences determined according to the IMGT numbering system: CDRH1 (GDSITIGF, SEQ ID NO: 33), CDRH2 (INYSGSS, SEQ ID NO: 34), CDRH3 (ARSGTDLDY, SEQ ID NO: 35); and the light chain variable region has three hypervariable regions containing the following amino acid sequences determined according to the IMGT numbering system: CDRL1 (QSLLDSDGKTY, SEQ ID NO: 36), CDRL2 (LVS), CDRL3 (WQGTHFPRT, SEQ ID NO: 37).

In a specific embodiment of the present disclosure, the antibody is 9D7, with a heavy chain amino acid sequence (SEQ ID NO: 7):

```
E V K L E E S G P S L V K P S Q T L S L T C S V S

G D S I T I G F W N W I R K F P G N K L E Y M G Y

I N Y S G S S Y Y N P S L K S R I S I T R D T S K

N Q Y Y L Q L N S V T P E D T A T Y Y C A R S G T

D L D Y W G Q G T T L T V S S;
``` and a light chain amino acid sequence (SEQ ID NO: 8):

```
D I V L T Q S P L T L S V T I G Q P A S I S C K S

S Q S L L D S D G K T Y L N W L L Q R P G Q S P K

R L I Y L V S K L D S G V P D R F T G S G S G T D

F T L K I S R V E A E D L G V Y Y C W Q G T H F P

R T F G G G T K L E I K R.
```

The sequences of the hypervariable regions on the heavy and light chains of the antibody determined according to the IMGT numbering system are underlined.

According to an embodiment of the present disclosure, the heavy chain amino acid sequence shown in SEQ ID NO: 7 is encoded by the nucleotide sequence (SEQ ID NO: 15):

```
GAGGTGAAGCTGGAGGAGTCAGGACCTAGCCTCGTGAAACCTTCTCAGAC

TCTGTCCCTCACCTGTTCTGTCTCTGGCGACTCCATCACCATTGGTTTCT

GGAACTGGATCCGGAAATTCCCAGGAAATAAACTTGAGTACATGGGATAC

ATAAACTACAGTGGTAGCAGTTACTACAATCCATCTCTCAAAAGTCGAAT

CTCCATCACTCGAGACACATCCAAGAACCAGTATTACCTGCAGTTGAATT

CTGTGACTCCTGAGGACACAGCCACATATTACTGTGCAAGATCTGGGACG

GACCTTGACTACTGGGGCCAAGGCACCACTCTCACAGTCTCCTCA.
```

According to an embodiment of the present disclosure, the light chain amino acid sequence shown in SEQ ID NO: 8 is encoded by the nucleotide sequence (SEQ ID NO: 16):

```
GATATTGTGCTCACACAGTCTCCACTCACTTTGTCGGTTACCATTGGACA

ACCAGCCTCCATCTCTTGCAAGTCAAGTCAGAGCCTCTTAGATAGTGATG

GAAAGACATATTTGAATTGGTTGTTACAGAGGCCAGGCCAGTCTCCAAAG

CGCCTAATCTATCTGGTGTCTAAACTGGACTCTGGAGTCCCTGACAGGTT

CACTGGCAGTGGATCAGGGACAGATTTCACACTGAAAATCAGCAGAGTGG

AGGCTGAGGATTTGGGAGTTTATTATTGCTGGCAAGGTACACATTTTCCT

CGGACGTTCGGTGGAGGCACCAAGCTGGAAATCAAACGG
```

According to an embodiment of the present disclosure, the anti-OX40 antibody may also include a sequence with 90% or more homology, preferably 95% or more homology, more preferably 98% or more homology, and even more preferably 99% or more homology with any of the amino acid sequence of antibodies 9C12, 1D9, 8A7 and 9D7. For example, the anti-OX40 antibody may have one conservative amino acid substitution, two amino acid conservative substitutions, or three conservative amino acid substitutions, or even more conservative amino acid substitutions compared with any of the amino acid sequence of antibodies 9C12, 1D9, 8A7 and 9D7.

The anti-OX40 antibody herein can also be made into a part of a kit or other diagnostic reagents as needed. The kit may include any one or more of: antagonist, anti-OX40 antibody or drug reference; protein purification column; immunoglobulin affinity purification buffer; cell assay diluent; instructions or literature, etc. The anti-OX40 antibodies may be used in different types of diagnostic tests, for example, they may be used to detect the presence of various diseases or drugs, toxins or other proteins in vitro or in vivo. For example, they may be used to detect serum or blood from a subject to test related diseases. Such related diseases may include OX40 related diseases, such as various cancers, inflammatory symptoms, or autoimmune diseases. Of course, the antibodies provided herein may also be used for radioimmunoassay and radioimmunotherapy of cancer.

The examples of the present disclosure are described in detail below. It should be noted that the examples described below are exemplary, and are only used to explain the present disclosure, and should not be understood as a limitation to the present disclosure. In addition, if not explicitly stated, all reagents used in the following examples are commercially available, or can be synthesized according to the text or known methods. The reaction conditions not listed are also easily obtained by those skilled in the art.

Example 1 Establishment of OX40 Hybridoma Cell Line

According to the full-length amino acid sequence of hOX40, the human fusion protein hOX40-HIS with the following amino acid sequence was prepared according to molecular biology methods:

(SEQ ID NO: 17)
LSTVTGLHCVGDTYPSNDRCCHECRPGNGMVSRCSRSQNTVCRPCGPGFY

NDVVSSKPCKPCTWCNLRSGSERKQLCTATQDTVCRCRAGTQPLDSYKPG

VDCAPCPPGHFSPGDNQACKPWTNCTLAGKHTLQPASNSSDAICEDRDPP

ATQPQETQGPPARPITVQPTEAWPRTSQGPSTRPVEVPGGRAVAHHHHH

H.

Then, the prepared hOX40-HIS fusion protein was used as an antigen, supplemented with an adjuvant to immunize mice to obtain monoclonal antibodies specifically binding to the hOX40 protein and hybridoma cell lines. The procedure is as follows:

1. Mice Immunization and Cell Fusion

The prepared hOX40-HIS fusion protein used as an antigen was dissolved in PBS to obtain a protein solution. An appropriate amount of the protein solution was mixed and emulsified with Freund's complete adjuvant (Sigma), and 4-week-old BALB/c female mice were injected subcutaneously with the antigen at multiple points. After 2 weeks, an appropriate amount of the protein solution was mixed and emulsified with Freund's incomplete adjuvant (Sigma), and the mice were subcutaneously immunized for the second time. Afterwards, the third and fourth immunizations were carried out every 3 weeks. Three days after the fourth immunization, the spleen was removed for cell fusion.

When the cells to be fused were cultured to the 5th-10th day, the culture supernatant with cloned cell clusters in the wells of the 96-well culture plate was sucked out and the antibody content was detected by the enzyme-linked immunosorbent assay. According to the secretion of antibodies, high-titer and high-specific cell lines were screened out.

The selected cell lines were subcloned, so as to obtain a stable cell line secreting monoclonal antibodies that specifically bind to the hOX40 protein.

The obtained stable cell line was cultured with fetal bovine serum containing low 10% IgG After 7-10 days of culture, the cell culture supernatant was collected and purified for antibody using Hi-Trap protein A HP (GE Healthcare) affinity chromatography column, to obtain the corresponding hybridoma antibody. The purified hybridoma antibody was directly used in subsequent experiments.

The hybridoma antibody includes the following four types through amino acid sequence determination, namely:

antibody 9C12, with the heavy chain amino acid sequence of SEQ ID NO:1, and the light chain amino acid sequence of SEQ ID NO:2;

antibody 1D9, with the heavy chain amino acid sequence of SEQ ID NO:3, and the light chain amino acid sequence of SEQ ID NO:4;

antibody 8A7, with the heavy chain amino acid sequence of SEQ ID NO:5, and the light chain amino acid sequence of SEQ ID NO:6; and antibody 9D7, with the heavy chain amino acid sequence of SEQ ID NO:7, and the light chain amino acid sequence of SEQ ID NO:8.

Example 2 Acquisition of cDNA Sequence of hOX40 Hybridoma Cell Lines

The total RNA of the hybridoma cell lines was extracted by Trizol (Invitrogen) method, and then reverse transcribed into cDNA with oligo-dT primer and SuperScript II Reverse Transcriptase (Invitrogen, catalog number: 18064-014). The DNA fragments of the heavy and light chains of the different antibodies in Example 1 were obtained by PCR amplification, linked to cloning vectors, and the clones were picked for sequencing. The sequencing results were compared to verify the correct sequence.

The nucleotide sequence of the heavy chain of antibody 9C12 obtained by PCR amplification is shown in SEQ ID NO: 9; and the nucleotide sequence of the light chain is shown in SEQ ID NO: 10.

The nucleotide sequence of the heavy chain of antibody 1D9 obtained by PCR amplification is shown in SEQ ID NO: 11, and the nucleotide sequence of the light chain is shown in SEQ ID NO: 12.

The nucleotide sequence of the heavy chain of antibody 8A7 obtained by PCR amplification is shown in SEQ ID NO: 13; and the nucleotide sequence of the light chain is shown in SEQ ID NO: 14.

The nucleotide sequence of the heavy chain of antibody 9D7 obtained by PCR amplification is shown in SEQ ID NO: 15; and the nucleotide sequence of the light chain is shown in SEQ ID NO: 16.

Example 3 Detection of hOX40 Specific Antibodies by ELISA Method

For the hybridoma antibodies prepared in Example 1, the specific binding of different antibodies to hOX40 was detected by the following steps:

1) coating of antigen: preparing hOX40-HIS antigen to a concentration of 0.6 μg/ml, adding at 100 μl/well, and coating overnight at 4° C.;

2) blocking with 1% BSA (diluted in PBS) at 37° C. for 2 hours, washing 3 times with 1× PBST (Tween-20, 1%), and patting dry gently;

3) addition of the primary antibody: preparing the four antibodies to a concentration of 2 μg/ml, and diluting 1:5 from the 2 μg/ml as the starting concentration to 7 gradient concentrations (that is, the concentrations of 2μg/ml, 400 ng/ml, 80 ng/ml, 16 ng/ml, 3.2 ng/ml, 0.64 ng/ml, 0.128 ng/ml, respectively). The prepared primary antibodies were added individually, and incubated at 30° C. for 1 hour; PBS was used as the blank control group;

4) addition of secondary antibody: washing with PBST 3 times, patting dry gently, adding 1:5000 diluted HRP enzyme-labeled goat anti-mouse IgG (H+L) secondary antibody, 100 μl per well, and incubating at 37° C. for 1 hour;

5) color development: washing with PBST 3 times, patting dry gently; adding TMB color reagent, 100 μl per well, for reacting at room temperature for 5-15 min;

6) color development stop: adding 2 M H2SO 4 solution 50 μl/well to stop the color reaction;

7) reading: using absorbance at 450 nm to detect the absorbance of each well on the microplate reader.

The ELISA test results are shown in Table 1, in which, the $EC_{50}$ value represents the half-maximal effect concentration, that is, the concentration that can cause 50% of the maximum effect. It can be seen from Table 1 that all the four monoclonal antibodies specifically bind to hOX40, with binding forces ranging from 10.8 nM to 0.017 nM. Compared with 1D9 antibody, 9C12 antibody, 8A7 antibody and 9D7 antibody exhibit better specific binding effect.

It can be seen from the above values that 9C12 antibody binds to hOX40-HIS antigen more easily than 8A7 antibody.

TABLE 1

ELISA results of monoclonal antibody binding to hOX40

| ng/ml | 9C12 | | 8A7 | | 9D7 | | 1D9 | |
|---|---|---|---|---|---|---|---|---|
| 2000 | 2.72 | 2.679 | 1.933 | 1.984 | 2.957 | 3.08 | 2.948 | 3.081 |
| 400 | 2.591 | 2.524 | 1.64 | 1.656 | 2.859 | 2.938 | 1.109 | 1.119 |
| 80 | 2.593 | 2.507 | 0.894 | 0.87 | 2.722 | 2.809 | 0.316 | 0.287 |
| 16 | 2.402 | 2.253 | 0.272 | 0.288 | 2.036 | 2.069 | 0.104 | 0.123 |
| 3.2 | 1.584 | 1.506 | 0.096 | 0.094 | 0.445 | 0.542 | 0.061 | 0.066 |
| 0.64 | 0.464 | 0.464 | 0.059 | 0.058 | 0.193 | 0.151 | 0.051 | 0.053 |
| 0.128 | 0.147 | 0.138 | 0.05 | 0.056 | 0.076 | 0.074 | 0.053 | 0.052 |
| 0 | 0.057 | 0.051 | 0.051 | 0.052 | 0.054 | 0.051 | 0.06 | 0.06 |
| $EC_{50}$ (nM) | 0.017 | | 0.727 | | 0.065 | | 10.8 | |

Example 4 Determination of the Kinetic Parameters of OX40 Antibody using ProteOn XPR Molecular Interaction Instrument The ProteOn XPR molecular interaction instrument may be used to detect the kinetics and affinity constants of the interaction between different drugs and a variety of different target proteins. 250 nM hOX40-HIS antigen (histone-modified hOX40 antigen) was immobilized on the surface of the GLM chip, and after equilibrating in PBST, was allowed to bind to the antibody 9C12 diluted twice in PBST to the concentration of 50, 25, 12.5, 6.25, 3.125, 0 nM, respectively, and then dissociated in PBST. The same detection method was used to detect the 8A7 antibody at concentrations of 308, 154, 77, 38.5, 19.25, 0 nM, respectively.

Figure 2:
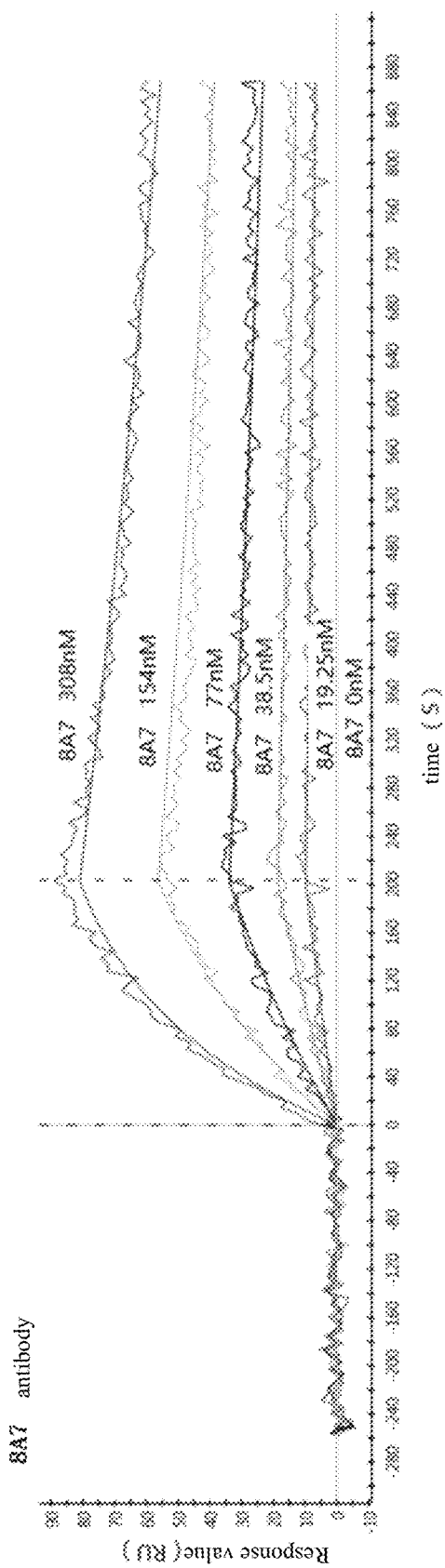
FIG. 2 is a graph showing the kinetic parameters of the 8A7 antibody according to an embodiment of the present disclosure.

The experimentally measured kinetic parameters of 9C12 and 8A7 are shown in Table 2, and the results are shown in FIG. 1 and FIG. 2.

TABLE 2

Kinetic parameters of different antibodies

| | Ligand: hOX40-HIS 250 nM | | | | |
|---|---|---|---|---|---|
| Antibody | ka (1/Ms) | kd (1/s) | KD (M) | Rmax | $Chi^2$ |
| 9C12 antibody | $4.45 \times 10^5$ | $6.73 \times 10^{-5}$ | $1.51 \times 10^{-10}$ | 218.91 | 13.59 |
| 8A7 antibody | $2.73 \times 10^4$ | $5.67 \times 10^4$ | $2.08 \times 10^{-8}$ | 103.22 | 4.77 |

In Table 2, ka(1/Ms) represents the binding rate constant, kd represents the dissociation rate constant, KD represents the equilibrium constant, Rmax represents the maximum binding capacity of the chip surface, and $Chi^2$ represents Chi-square test value. The association rate constant and the dissociation rate constant represent the degree of difficulty of the binding of the antigen to the antibody.

Example 5 Species-specific Study of OX40 Antibody

Human OX40 antigen, monkey OX40 antigen and murine OX40 antigen were used for coating respectively to detect whether OX40 antibody cross-reacts with OX40 protein of different species, through the following steps:

1) coating of antigen: preparing human OX40 antigen, monkey OX40 antigen, and murine OX40 antigen to a concentration of 0.25 µg/ml, adding at 100 µl/well, and coating overnight at 4° C.;

2) blocking with 1% BSA (diluted in PBS) at 37° C. for 2 hours, washing 3 times with 1× PBST (Tween-20, 1%), and patting dry gently;

3) addition of the primary antibody: preparing antibody 9C12 to a concentration of 2 µg/ml, and diluting 1:5 from the 2 µg/ml as the starting concentration to the four antibodies 7 gradient concentrations (that is, the concentrations of 2 µg/ml, 400 ng/ml, 80 ng/ml, 16 ng/ml, 3.2 ng/ml, 0.64 ng/ml, 0.128 ng/ml, respectively). PBS was used as the blank control group. The prepared primary antibodies were added individually, and incubated at 30° C. for 1 hour;

4) addition of secondary antibody: washing with PBST 3 times, patting dry gently, adding 1:5000 diluted HRP enzyme-labeled goat anti-mouse IgG (H+L) secondary antibody, 100 µl per well, and incubating at 37° C. for 1 hour;

5) color development: washing with PBST 3 times, patting dry gently; adding TMB color reagent, 100 µl per well, for reacting at room temperature for 5-15 min;

6) color development stop: adding 2 M H2SO4 solution 50 µl/well to stop the color reaction;

7) reading: using absorbance 450 nm to detect the absorbance of each well on the microplate reader.

Figure 3:
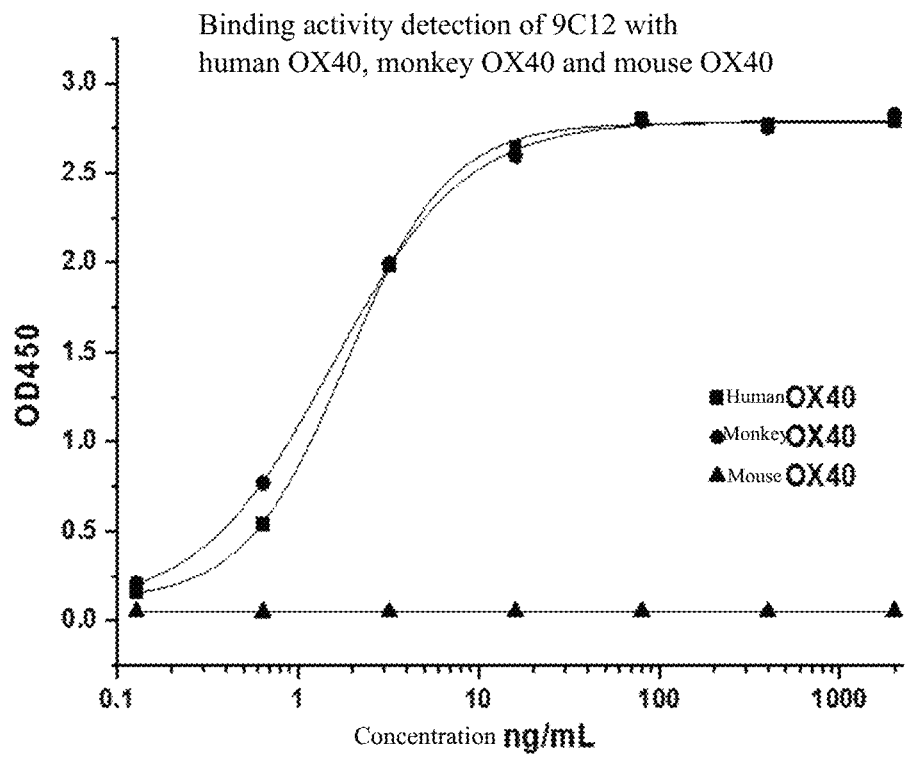
FIG. 3 is a graph showing the ELISA results of the species-specific binding according to an embodiment of the present disclosure.

The results are shown in Table 3 and FIG. 3. The 9C12 antibody binds to human OX40 antigen and monkey OX40 antigen with similar affinity, and does not cross-react with murine OX40 antigen.

TABLE 3

ELISA results of species-specific binding

| Con. of 9C12 antibody ng/ml | Huan OX40-HIS antigen | | Monkey OX40-HIS antigen | | Murine OX40 antigen | |
|---|---|---|---|---|---|---|
| 2000 | 2.808 | 2.775 | 2.839 | 2.81 | 0.053 | 0.054 |
| 400 | 2.84 | 2.693 | 2.731 | 2.778 | 0.05 | 0.051 |
| 80 | 2.841 | 2.762 | 2.741 | 2.836 | 0.049 | 0.052 |
| 16 | 2.705 | 2.591 | 2.553 | 2.636 | 0.047 | 0.05 |
| 3.2 | 1.953 | 2.012 | 2.043 | 1.95 | 0.048 | 0.051 |

TABLE 3-continued

ELISA results of species-specific binding

| Con. of 9C12 antibody ng/ml | Human OX40-HIS antigen | | Monkey OX40-HIS antigen | | Murine OX40 antigen | |
|---|---|---|---|---|---|---|
| 0.64 | 0.533 | 0.551 | 0.776 | 0.761 | 0.047 | 0.049 |
| 0.128 | 0.162 | 0.157 | 0.212 | 0.211 | 0.049 | 0.051 |
| 0 | 0.048 | 0.046 | 0.046 | 0.047 | 0.046 | 0.05 |
| $EC_{50}$ (nM) | 0.012 | | 0.010 | | \ | |

Example 6 Detection of the Binding Activity of 9C12 with hOX40 by FACS (Fluorescence Activated Cell Sorting) Method In this experiment, 293T-OX40 stably transfected cell lines were used as the experimental cells, and the FACS method was used to detect the binding of 9C12 to the hOX40 protein on the cell membrane surface. The specific procedure is as follows:

293T cells expressing hOX40 were digested, and prepared to a final concentration of $10^6$ cells/ml. 100 µl of cell suspension from each group was added into a 1.5 ml EP tube. Various concentrations of 9C12 antibody (10000 ng/ml, 4000 ng/ml, 2000 ng/ml, 1000 ng/ml, 500 ng/ml, 200 ng/ml, 20 ng/ml, 2 ng/ml) were added, and incubated on ice for 1 hour. After 1 hour, the tube was washed with HBSS once. Each group was added with prepared APC goat anti-human IgG secondary antibody, incubated on ice for 20 minutes in the dark, washed once with HBSS, and finally suspended with 200 µl of HBSS, and the cells were tested.

Figure 4:
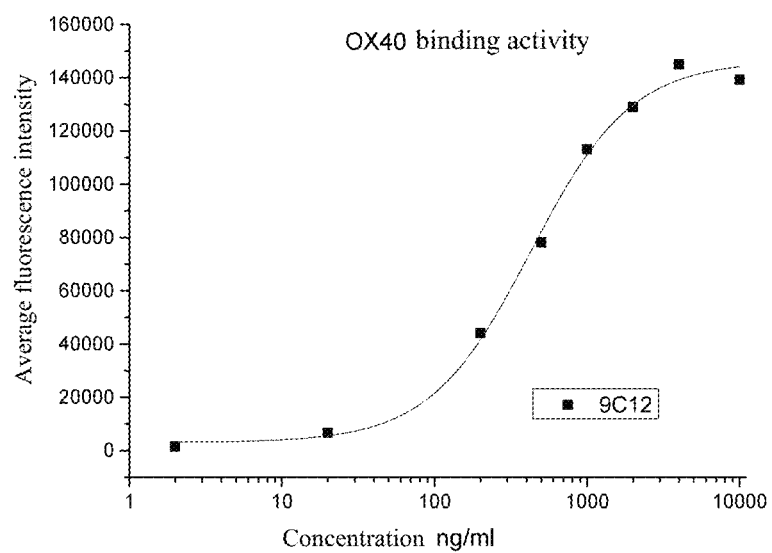
FIG. 4 is a graph showing the results of detecting the binding activity of 9C12 with OX40 according to the FACS method of an embodiment of the present disclosure.

The binding activity of 9C12 with hOX40 on the cell membrane surface was detected by the FACS method, and the results are shown in FIG. 4 and Table 4 below.

TABLE 4 results of the binding activity of 9C12 with hOX40 detected by FACS method

| Con. | Average fluorescence intensity | | | | | | | | $EC_{50}$ |
|---|---|---|---|---|---|---|---|---|---|
| (ng/ml) | 10000 | 4000 | 2000 | 1000 | 500 | 200 | 20 | 2 | (nM) |
| 9C12 | 139266.4 | 145072.4 | 128990.6 | 113145.7 | 78203.3 | 44152.3 | 6624.4 | 1498.5 | 2.84 |

As seen from FIG. 4 and on the statistical results in the above Table, 9C12 antibody binds to hOX40 on the surface of the cell membrane with $EC_{50}$ of 2.84 nM.

Example 7 Study on Co-stimulation of Human Primary CD4+ T cells with OX40 Antibody In Vitro 40 ml of fresh human blood was used to separate human PBMC with lymphocyte separation fluid. CD14 monocytes were first positively selected by CD14 magnetic beads (Miltenyi, catalog number: 130-050-201), and the remaining cells were separated by CD4 negative selection magnetic beads (Miltenyi, catalog number: 130-096-533) to isolate CD4+ T cells. CD4+ T cells were added with 2 µg/ml PHA-L (Sigma) and 200 IU/ml human recombinant IL-2 (R&D), plated into a six-well plate at $1 \times 10^6$ cells/well in PBMC complete medium (90% RPMI 1640 (Hyclone) +10% FBS (Sijiqing)), and incubated in an incubator at 37° C. under 5% $CO_2$ for 48 hours.

On the next day, 100 µl of PBS solution containing 2 µg/ml goat anti-mouse Fcγ specific IgG (Jackson) (or 2 µg/ml goat anti-mouse Fcγ specific IgG plus 2 µg/ml goat anti-human Fcγ specific IgG (Jackson)) was added to each well of a 96-well plate. The plate was incubated in a refrigerator at 4° C. for coating overnight. The next day, the supernatant was removed and washed with PBS. 100 µl of PBS solution containing 1% BSA was added to each well, and the plate was blocked in an incubator at 37° C. under 5% $CO_2$ for 90 min. After completion, the supernatant from each well was removed again, and 200 µl of PBS solution was added for washing and set aside.

The CD4+ T cells were recovered and centrifuged at 1800 rpm for 5 minutes, then resuspended in PBMC complete medium, and the cell concentration was adjusted to $1 \times 10^6$ cells/ml. The suspension was added to coated wells, with 100 µl per well, then 50 µl of CD3 antibody OKT3 (2 ng/ml, Biolegend) and 50 µl of OX40 antibody of different concentrations (from 1 µg/ml 10 times diluted to 1 ng/ml) or 50 µl of PBMC complete medium were added and mixed well. The plate was incubated in an incubator at 37° C. under 5% $CO_2$ for 72 hours.

The supernatant was harvested 72 hours later, and the expression of IFN-γ in the supernatant was detected using an IFN-γELISA detection kit (Dayou, catalog number: DKW12-1000-096).

Figure 5:
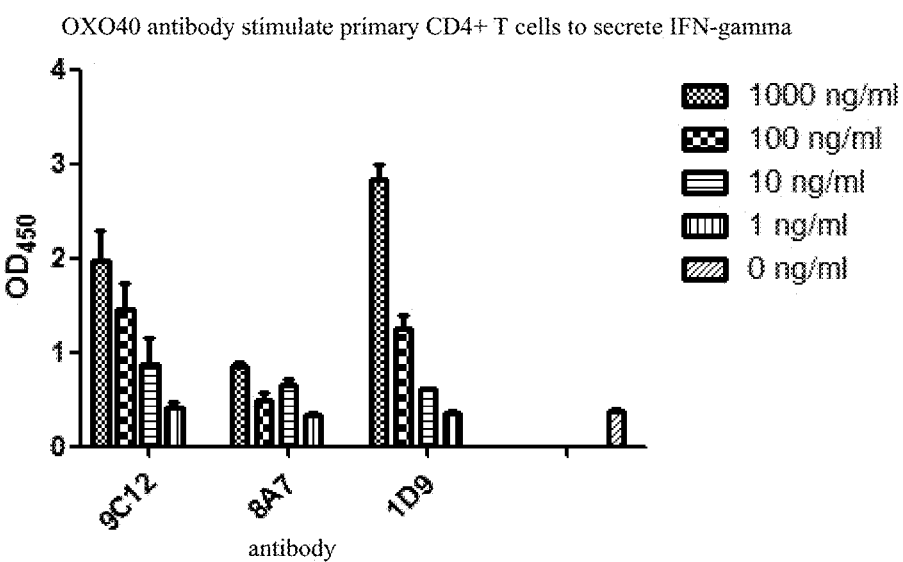
FIG. 5 is a graph showing the results of OX40 antibody stimulating primary CD4+ T cells to secrete IFN-γ according to an embodiment of the present disclosure.

As shown in FIG. 5, the OX40 antibody has the ability to stimulate human primary CD4+ T cells and can promote the expression of IFN-γ.

Example 8 Detecting the Biological Activity of OX40 Antibody Based on 2-cell Luciferase Reporter Gene Method In this example, a set of 2-cell reporter genes were used for biological activity assays to evaluate the ability of OX40 antibodies for signal transduction through human OX40. The amount of T cell activation is measured by the overexpression of luciferase due to stimulation being able to respond to the NFKB signaling pathway. That is, the NFκB signaling pathway is stimulated by the OX40 antibody to generate the Jurkat-NFκB luciferase report. NFκB signaling occurs downstream of OX40 and can be correlated with other measures of T cell activation, such as proliferation and cytokine release. The amount of T cell activation can be measured by detecting the amount of luciferase.

The specific procedure is as follows:
Lentivirus was used to construct 293T cells (293T-CD32A) capable of stably expressing CD32A and Jurkat cells (Jurkat-NFκB-OX40) capable of stably expressing human OX40 and containing the firefly luciferase gene regulated by the NFκB signaling pathway. After trypsinization of 293T-CD32A cells, they were resuspended in complete medium and the cell concentration was adjusted to $2 \times 10^6$ cells/ml. Jurkat-NFκB-OX40 cells were centrifuged at 1800 rpm for 5 minutes and then resuspended in complete medium and the cell concentration was adjusted to $2 \times 10^6$ cells/ml.

In a 96-well, 50 μl of 293T-CD32A cell and Jurkat-NFκB-OX40 cell suspension was added to each well and mixed well. Then 100 μl of different concentrations of OX40 antibody (9C12 antibody and 1D9 antibody, the concentrations of 10 μg/ml, 1 μg/ml, 0.1 μg/ml, 0.01 μg/ml, 0.001 μg/ml) or 100 μl Jurkat cell complete medium containing 1 μg/ml puromycin were added and mixed well. They were incubated in an incubator at 37° C. under 5% $CO_2$ overnight for 20 hours.

The next day, the mixture was centrifuged at 1800 rpm for 5 minutes and the supernatant was discarded. 100 μl of lysate of firefly luciferase detection kit (Biyuntian, catalog number: RG005) was added to each well, shaken on a shaker at room temperature for 30 minutes to lyse cells and release luciferase. After centrifugation at 2000 rpm for 5 minutes, 90 μl of supernatant was removed from each well and added to a white opaque 96-well plate (Costar). After adding 100 μl of color developing solution to the supernatant of each well, it was placed in a fully functional microplate detector (PerkinElmer, model: EnVision) to detect the self-luminous intensity.

Figure 6:
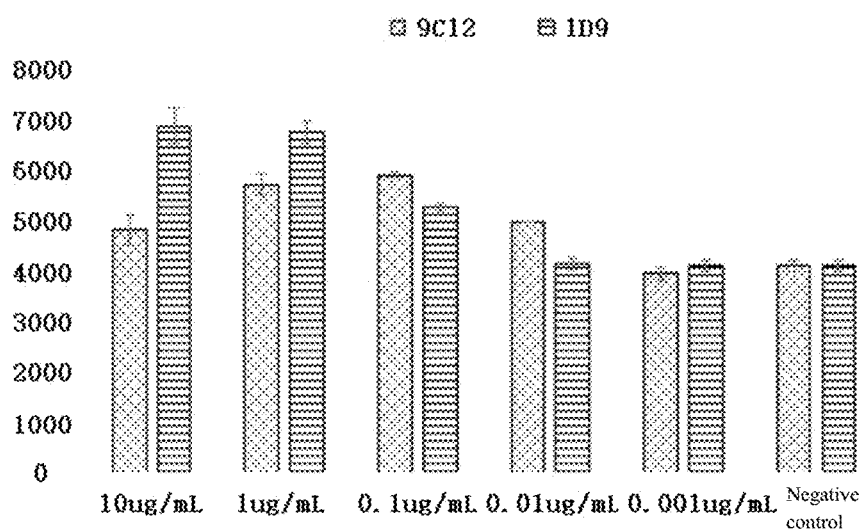
FIG. 6 is a graph showing the results of detecting OX40 antibody activity by the Jurkat-NFκB-OX40 reporter gene method for OX40 according to an embodiment of the present disclosure.

The results are shown in FIG. 6, and show that both the 9C12 antibody and the 1D9 antibody have a significant stimulating effect on the Jurkat-NFKB-OX40 reporter cells expressing human OX40.

Example 9 Anti-tumor Effect of OX40 Antibody in MC38 Mouse Colorectal Cancer B-hOX40 Humanized Mouse Model The specific procedure is as follows.

MC38 cells are murine colon cancer cells derived from C57BL/6 mice and were purchased from Shun Ran Shanghai Biotechnology Co., Ltd. B-hOX40 humanized mice are mouse models in which the mouse-derived OX40 protein molecule that interacts with the OX4OL protein molecule in C57BL/6 mice is partially replaced with a human-derived protein through genetic engineering technology, and were purchased from Biocytogen Jiangsu Co., Ltd.

MC38 cells resuspended in PBS were inoculated subcutaneously in the right flank of B-h OX40 humanized mice at a concentration of $5 \times 10^5$ cells/0.1 mL and a volume of 0.1 mL/animal. When the average tumor volume reaches 100-150 $mm^3$, mice with moderate tumor volume and weight were selected, and distributed evenly into 4 experimental groups, 5 mice in each group. The administration was started on the day of grouping, and the specific dosing schedule is shown in the following table. The G1 group was given PBS as the control group.

TABLE 5

Pharmacodynamic experiment design

| Group | Drugs | No. of animals (N) | Dose (mg/kg)[a] | Route of administration | Dosing frequency[b] | No. of dosing |
|---|---|---|---|---|---|---|
| G1 | PBS | 5 | — | Intravenous(i.p.) | BIW | 6 |
| G2 | 8A7Ab | 5 | 3 | Intravenous(i.p.) | BIW | 6 |
| G3 | 1D9Ab | 5 | 3 | Intravenous(i.p.) | BIW | 6 |
| G4 | 9C12 Ab | 5 | 3 | Intravenous(i.p.) | BIW | 6 |

Note:
[a]The administration volume is calculated as 10 μL/g based on the weight of the experimental animal;
[b]BIW means dosing twice a week.

Table 6 shows the tumor growth inhibition in tumor-bearing mice in each treatment group.

TABLE 6

Tumor growth inhibitory effect

| Group | Drugs | Tumor volume on day 0 ($mm^3$) | Tumor volume on day 23 ($mm^3$) | TGI (%) | P value |
|---|---|---|---|---|---|
| G1 | PBS | 118 ± 15 | 1884 ± 364 | — | — |
| G2 | 8A7 Ab | 49 ± 57 | 800 ± 871 | 57.44 | 0.289 |
| G3 | 1D9 Ab | 114 ± 13 | 894 ± 461 | 55.84 | <0.05 |
| G4 | 9C12 Ab | 118 ± 13 | 789 ± 569 | 61.97 | <0.05 |

In Table 6, TGI (The tumor growth inhibition value) represents the tumor volume inhibition rate, and is used to evaluate the inhibitory effect of drugs on tumor growth in animals. The TGI value is calculated as follows:

$$TGI \text{ value } (\%) = (1 - \text{relative tumor volume of experimental group/relative tumor volume of control group}) \times 100\%$$

The relative tumor volume is the change value of the tumor volume after a period of drug treatment.

Taking the G2 group as an example, the TGI value is calculated as follows: the tumor volume change value of the G2 group on day 23 is divided by the tumor volume change value of the control group on day 23 to obtain the difference, and then the difference is subtracted from 1 to obtain the TGI value.

It can be seen from Table 6 that whether the 8A7 antibody, the 1D9 antibody or the 9C12 antibody are used, they all show a good tumor inhibition rate. In particular, the 9C12 antibody shows a higher tumor inhibition rate and a better therapeutic effect.

Figure 7:
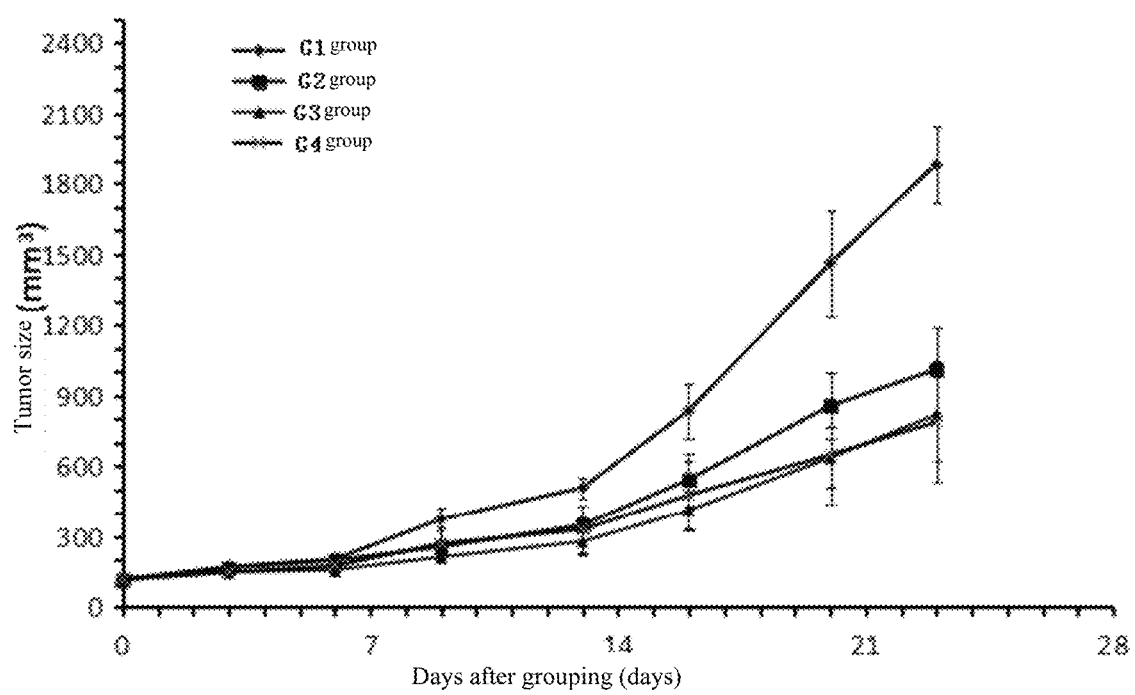
FIG. 7 is a graph showing the changes of tumor volume of experimental animals according to an embodiment of the present disclosure.

FIG. 7 shows the tumor volume in tumor-bearing mice measured at different times, that is, the tumor growth curves of mice treated with different drugs. It can be seen from FIG. 7 that, compared with the PBS control group, the 8A7 antibody treatment, the 1D9 antibody treatment, or the 9C12 antibody treatment all showed significant suppression of tumor volume in mice. In addition, compared with 8A7 antibody, 1D9 antibody and 9C12 antibody showed higher tumor suppressive effect.

Herein, the terms "first" and "second" are only used for descriptive purposes, and cannot be understood as indicating or implying relative importance or implicitly indicating the number of indicated technical features. Therefore, the features defined with "first" and "second" may explicitly or implicitly include at least one of the features. In the description of the present disclosure, "plurality" means at least two, such as two, three, etc., unless otherwise specifically defined.

In the description of this specification, descriptions with reference to the terms "one embodiment", "some embodiments", "examples", "specific examples", or "some examples" etc. mean that the specific features, structures, materials, or characteristics described in conjunction with the embodiments or examples include in at least one embodiment or example of the present disclosure. In this specification, the schematic representations of the above-mentioned terms are not necessarily directed to the same embodiment or example. Moreover, the described specific features, structures, materials or characteristics can be combined in any one or more embodiments or examples in a suitable manner. In addition, those skilled in the art can combine the different embodiments or examples and the features of the different embodiments or examples described in this specification without contradicting each other.

Although the embodiments of the present disclosure have been shown and described above, it can be understood that the above-mentioned embodiments are exemplary and should not be construed as limiting the present disclosure. Those of ordinary skill in the art can comment on the above-mentioned embodiments within the scope of the present disclosure. The embodiment undergoes changes, modifications, substitutions, and modifications.

What is claimed is:

1. An anti-OX40 antibody or antigen-binding fragment thereof, comprising at least one of:

(1) a heavy chain variable region comprising amino acid sequences of SEQ ID NO: 18, SEQ ID NO: 19 and SEQ ID NO: 20, and a light chain variable region comprising amino acid sequences of SEQ ID NO: 21, AAT and SEQ ID NO: 22;

(2) a heavy chain variable region comprising amino acid sequences of SEQ ID NO: 23, SEQ ID NO: 24 and SEQ ID NO: 25, and a light chain variable region comprising amino acid sequences of SEQ ID NO: 26, YTS and SEQ ID NO: 27;

(3) a heavy chain variable region comprising amino acid sequences of SEQ ID NO: 28, SEQ ID NO: 29 and SEQ ID NO: 30, and a light chain variable region comprising amino acid sequences of SEQ ID NO: 31, WAS and SEQ ID NO: 32; and (4) a heavy chain variable region comprising amino acid sequences of SEQ ID NO: 33, SEQ ID NO: 34 and SEQ ID NO: 35, and a light chain variable region comprising amino acid sequences of SEQ ID NO: 36, LVS and SEQ ID NO: 37.

2. The antibody or antigen-binding fragment thereof according to claim 1, comprising at least one of:

(a) a heavy chain comprising the amino acid sequence shown in SEQ ID NO: 1 and a light chain comprising the amino acid sequence shown in SEQ ID NO: 2;

(b) a heavy chain comprising the amino acid sequence shown in SEQ ID NO: 3 and a light chain comprising the amino acid sequence shown in SEQ ID NO: 4;

(c) a heavy chain comprising the amino acid sequence shown in SEQ ID NO: 5 and a light chain comprising the amino acid sequence shown in SEQ ID NO: 6;
(d) a heavy chain comprising the amino acid sequence shown in SEQ ID NO: 7 and a light chain comprising the amino acid sequence shown in SEQ ID NO: 8; and
(e) any of (a) to (d) with one or more conservative amino acid substitutions in an amino acid region other than the heavy chain variable region and the light chain variable region.

3. The antibody or antigen-binding fragment thereof according to claim 2, wherein the antibody is a monoclonal antibody,
the antibody or antigen-binding fragment thereof has a sequence with 90% or more homology with any of (a) to (d), wherein CDRs of the antibody or antigen-binding fragment thereof are not modified.

4. An isolated polynucleotide, encoding an antibody or antigen-binding fragment thereof according to claim 1.

5. The polynucleotide according to claim 4, wherein the polynucleotide comprises at least one of:
the nucleotide sequence shown in SEQ ID NO: 9 and the nucleotide sequence shown in SEQ ID NO: 10;
the nucleotide sequence shown in SEQ ID NO: 11 and the nucleotide sequence shown in SEQ ID NO: 12;
the nucleotide sequence shown in SEQ ID NO: 13 and the nucleotide sequence shown in SEQ ID NO: 14; and
the nucleotide sequence shown in SEQ ID NO: 15 and the nucleotide sequence shown in SEQ ID NO: 16.

6. An expression vector, comprising a polynucleotide according to claim 4.

7. The expression vector according to claim 6, further comprising:
a control element operably linked to the polynucleotide for controlling the expression of the polynucleotide in a host cell,
wherein the control element comprises at least one of a promoter, an enhancer, and a terminator.

8. The expression vector according to claim 7, wherein the host cell is a mammalian cell.

9. A recombinant cell comprising an expression vector according to claim 6.

10. A method for preparing an antibody or antigen-binding fragment thereof according to claim 1, comprising culturing a recombinant cell comprising an expression vector,
wherein the expression vector comprises a polynucleotide encoding an antibody or antigen-binding fragment thereof according to claim 1.

11. A hybridoma cell, at least one selected from:
hybridoma cell HX011-9C12, deposited in the China Center for Type Culture Collection with a deposit number C2018197 on Sep. 27, 2018; and
hybridoma cell HX011-1D9, deposited in the China Center for Type Culture Collection with a deposit number C2018198 on Sep. 27, 2018.

12. A pharmaceutical composition, comprising: an antibody or antigen-binding fragment thereof according to claim 1.

13. A method for identifying a drug capable of binding to OX40, comprising:
contacting an antibody or antigen-binding fragment thereof according to claim 1 with an antigen in the presence of a candidate drug, and determining a first binding amount of the antibody or antigen-binding fragment thereof to the antigen; and
contacting the antibody or antigen-binding fragment thereof according to claim 1 with the antigen in the absence of the candidate drug, and determining a second binding amount of the antibody or antigen-binding fragment thereof to the antigen;
wherein the antigen is OX40 or fragment thereof, and
the second binding amount greater than the first binding amount indicates that the candidate drug is capable of binding to OX40.

14. A drug combination, comprising:
(1) an antibody or antigen-binding fragment thereof according to claims 1; and
(2) an immune enhancing agent other than (1).

15. The drug combination according to claim 14, wherein the immune enhancing agent other than (1) is at least one selected from: an anti-PD1 antibody, an anti-LAG-3 antibody, an anti-CTLA-4 antibody, an anti-Tim3 antibody or an anti-PD-L1 antibody.

16. A method for treating autoimmune disease or cancer, comprising administering an antibody or antigen-binding fragment thereof according to claim 1 to a subject in need thereof.

17. The method for treating cancer according to claim 16, wherein the cancer is selected from breast cancer, prostate cancer, ovarian cancer, colorectal cancer or B-cell lymphoma.

18. The antibody or antigen-binding fragment thereof according to claim 1, comprising at least one of:
(1) a heavy chain variable region comprising amino acid sequences of SEQ ID NO: 18, SEQ ID NO: 19 and SEQ ID NO: 20, and a light chain variable region comprising amino acid sequences of SEQ ID NO: 21, AAT and SEQ ID NO: 22;
(2) a heavy chain variable region comprising amino acid sequences of SEQ ID NO: 23, SEQ ID NO: 24 and SEQ ID NO: 25, and a light chain variable region comprising amino acid sequences of SEQ ID NO: 26, YTS and SEQ ID NO: 27;
(3) a heavy chain variable region comprising amino acid sequences of SEQ ID NO: 28, SEQ ID NO: 29 and SEQ ID NO: 30, and a light chain variable region comprising amino acid sequences of SEQ ID NO: 31, WAS and SEQ ID NO: 32;
(4) a heavy chain variable region comprising amino acid sequences of SEQ ID NO: 33, SEQ ID NO: 34 and SEQ ID NO: 35, and a light chain variable region comprising amino acid sequences of SEQ ID NO: 36, LVS and SEQ ID NO: 37; and
(5) an amino acid sequence of any of (1) to (4) with one or more conservative amino acid and wherein CDRs of the antibody or antigen-binding fragment thereof are not modified.

19. The antibody or antigen-binding fragment thereof according to claim 1, comprising at least one of:
(a) a heavy chain comprising the amino acid sequence shown in SEQ ID NO: 1 and a light chain comprising the amino acid sequence shown in SEQ ID NO: 2;
(b) a heavy chain comprising the amino acid sequence shown in SEQ ID NO: 3 and a light chain comprising the amino acid sequence shown in SEQ ID NO: 4;
(c) a heavy chain comprising the amino acid sequence shown in SEQ ID NO: 5 and a light chain comprising the amino acid sequence shown in SEQ ID NO: 6; and
(d) a heavy chain comprising the amino acid sequence shown in SEQ ID NO: 7 and a light chain comprising the amino acid sequence shown in SEQ ID NO: 8.

* * * * *